United States Patent

Cupps et al.

[11] Patent Number: 5,804,587
[45] Date of Patent: *Sep. 8, 1998

[54] 6-(2-IMIDAZOLINYLAMINO) QUINOLINES USEFUL AS ALPHA-2 ADRENOCEPTOR AGONISTS

[75] Inventors: Thomas Lee Cupps, Oxford; Peter J. Maurer, Cincinnati; Jeffrey J. Ares, Hamilton; Raymond T. Henry, Pleasant Plain; Russell James Sheldon, Fairfield; Glen E. Mieling, West Chester; Sophie E. Bogdan, Maineville, all of Ohio

[73] Assignee: The Procter & Gamble Company, Cincinnati, Ohio

[ * ] Notice: The term of this patent shall not extend beyond the expiration date of Pat. No. 5,578,607.

[21] Appl. No.: 755,936

[22] Filed: Nov. 25, 1996

Related U.S. Application Data

[63] Continuation-in-part of Ser. No. 496,704, Jun. 29, 1995, Pat. No. 5,739,148.
[51] Int. Cl.⁶ .......................... C07D 403/12; A61H 31/47
[52] U.S. Cl. ............................................. 514/314; 546/171
[58] Field of Search .............................. 546/171; 514/314

[56] References Cited

U.S. PATENT DOCUMENTS 5,578,607 11/1996 Cupps et al. ........................... 514/314

*Primary Examiner*—Robert W. Ramsuer
*Assistant Examiner*—Ebenezer O. Sackey
*Attorney, Agent, or Firm*—Richard A. Hake; Milton B. Graff; David L. Suter

[57] ABSTRACT

The subject invention relates to compounds having the structure:

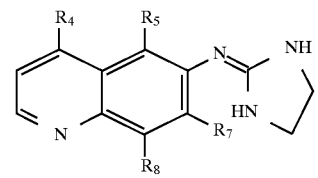

as defined in the claims, and to pharmaceutical compositions containing such compounds, and the use of such compounds for preventing or treating of disorders modulated by alpha-2 adrenoceptors.

36 Claims, No Drawings

6-(2-IMIDAZOLINYLAMINO) QUINOLINES USEFUL AS ALPHA-2 ADRENOCEPTOR AGONISTS

This is a continuation-in-part of application Ser. No. 08/496,704, filed on Jun. 29, 1995 now Pat. No. 5,739,148.

TECHNICAL FIELD

The subject invention relates to certain substituted 6-(2-imidazolinylamino)quinoline compounds. The compounds have been found to be alpha-2 adrenoceptor agonists and are useful for treatment of disorders modulated by alpha-2 adrenoceptors.

BACKGROUND OF THE INVENTION

Therapeutic indications of alpha-2 adrenoceptor agonists have been discussed in the literature: Ruffolo, R. R., A. J. Nichols, J. M. Stadel, & J. P. Hieble, "Pharmacologic and Therapeutic Applications of Alpha-2 Adrenoceptor Subtypes", *Annual Review of Pharmacology & Toxicology* Vol. 32 (1993) pp. 243–279.

Information regarding alpha adrenergic receptors, agonists and antagonists, in general, and regarding compounds related in structure to those of this invention are disclosed in the following references: Timmermans, P. B. M. W. M., A. T. Chiu & M. J. M. C. Thoolen, "12.1 α-Adrenergic Receptors", *Comprehensive Medicinal Chemistry*, Vol. 3, Membranes & Receptors, P. G. Sammes & J. B. Taylor, eds., Pergamon Press (1990), pp. 133–185; Timmermans, P. B. M. W. M. & P. A. van Zwieten, "α-Adrenoceptor Agonists and Antagonists", *Drugs of the Future*, Vol. 9, No. 1, (January, 1984), pp. 41–55; Megens, A. A. H. P., J. E. Leysen, F. H. L. Awouters & C. J. E. Niemegeers, "Further Validation of in vivo and in vitro Pharmacological Procedures for Assessing the $\alpha_1$ and $\alpha_2$-Selectivity of Test Compounds: (2) α-Adrenoceptor Agonists", *European Journal of Pharmacology*, Vol. 129 (1986), pp. 57–64; Timmermans, P. B. M. W. M., A. de Jonge, M. J. M. C. Thoolen, B. Wilffert, H. Batink & P. A. van Zwieten, "Quantitative Relationships between α-Adrenergic Activity and Binding Affinity of α-Adrenoceptor Agonists and Antagonists", *Journal of Medicinal Chemistry*, Vol. 27 (1984) pp. 495–503; van Meel, J. C. A., A. de Jonge, P. B. M. W. M. Timmermans & P. A. van Zwieten, "Selectivity of Some Alpha Adrenoceptor Agonists for Peripheral Alpha-1 and Alpha-2 Adrenoceptors in the Normotensive Rat", *The Journal of Pharmacology and Experimental Therapeutics*, Vol. 219, No. 3 (1981), pp. 760–767; Chapleo, C. B., J. C. Doxey, P. L. Myers, M. Myers, C. F. C. Smith & M. R. Stillings, "Effect of 1,4-Dioxanyl Substitution on the Adrenergic Activity of Some Standard α-Adrenoreceptor Agents", *European Journal of Medicinal Chemistry*, Vol. 24 (1989), pp. 619–622; Chapleo, C. B., R. C. M. Butler, D. C. England, P. L. Myers, A. G. Roach, C. F. C. Smith, M. R. Stillings & I. F. Tulloch, "Heteroaromatic Analogues of the $\alpha_2$-Adrenoreceptor Partial Agonist Clonidine", *Journal of Medicinal Chemistry*, Vol. 32 (1989), pp. 1627–1630; Clare, K. A., M. C. Scrutton & N. T. Thompson, "Effects of $\alpha_2$-Adrenoceptor Agonists and of Related Compounds on Aggregation of, and on Adenylate Cyclase Activity in, Human Platelets", *British Journal of Pharmacology*, Vol. 82 (1984), pp. 467–476; U.S. Pat. No. 3,890,319 issued to Danielewicz, Snarey & Thomas on Jun. 17, 1975; and U.S. Pat. No. 5,091,528 issued to Gluchowski on Feb. 25, 1992. However, many compounds related in structure to those of this invention do not provide the activity and specificity desirable when treating disorders modulated by alpha-2 adrenoceptors.

For example, many compounds found to be effective nasal decongestants are frequently found to have undesirable side effects, such as causing hypertension and insomnia at systemically effective doses. There is a need for new drugs which provide relief from nasal congestion without causing these undesirable side effects.

OBJECTS OF THE INVENTION

It is an object of the invention to provide compounds and compositions useful in treating disorders modulated by alpha-2 adrenoceptors.

It is an object of this invention to provide novel compounds having substantial activity in preventing or treating nasal congestion, otitis media, and sinusitis, without undesired side effects.

It is also an object of this invention to provide novel compounds for treating cough, chronic obstructive pulmonary disease (COPD) and/or asthma.

It is also an object of this invention to provide novel compounds for treating diseases and disorders associated with sympathetic nervous system activity, including benign prostatic hypertrophy, cardiovascular disorders comprising myocardial ischemia, cardiac reperfusion injury, angina, cardiac arrhythmia, heart failure and hypertension.

It is also an object of this invention to provide novel compounds for treating ocular disorders, such as ocular hypertension, glaucoma, hyperemia, conjunctivitis and uveitis.

It is also an object of this invention to provide novel compounds for treating gastrointestinal disorders, such as diarrhea, irritable bowel syndrome, hyperchlorhydria (hyperacidity) and peptic ulcer (ulcer).

It is also an object of this invention to provide novel compounds for treating migraine.

It is also an object of this invention to provide novel compounds for treating pain, substance abuse and/or withdrawal.

It is a still further object of this invention to provide such compounds which have good activity from peroral, parenteral, intranasal and/or topical dosing.

SUMMARY OF THE INVENTION

The subject invention relates to compounds having the structure:

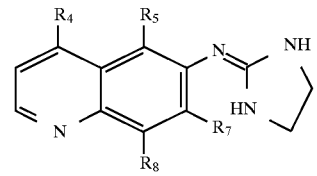

wherein:
(a) $R_4$ is selected from the group consisting of hydrogen; unsubstituted alkanyl or alkenyl having from 1 to about 3 carbon atoms; cycloalkyl; cycloalkenyl; methyl monosubstituted with hydroxy, thiol or amino; unsubstituted alkylthio or alkoxy having from 1 to about 3 carbon atoms; amino; unsubstituted amide; amido, unsubstituted or substituted with alkanyl or alkenyl having from 1 to about 3 carbon atoms; halo; unsubstituted sulfoxide; unsubstituted sulfonyl; and cyano.
(b) $R_5$ is unsubstituted alkanyl or alkenyl having from 1 to about 3 carbon atoms;

(c) $R_7$ is selected from hydrogen; unsubstituted $C_1$–$C_3$ alkanyl or alkenyl; hydroxy, thiol or amino; halo; and cyano;

(d) $R_8$ is selected from the group consisting of hydrogen unsubstituted alkanyl or alkenyl having from 1 to about 3 carbon atoms; unsubstituted alkylthio or alkoxy having from 1 to about 3 carbon atoms; hydroxy; thiol; and halo; and pharmaceutical compositions containing such compounds, and the use of such compounds for preventing or treating disorders modulated by alpha-2 adrenoceptors.

DETAILED DESCRIPTION OF THE INVENTION

As used herein, "alkyl" means a straight or branched hydrocarbon chain, saturated or unsaturated, unsubstituted or substituted. Unless otherwise specified, preferred alkyl is alkanyl or alkenyl as defined herein, especially alkanyl; preferred alkyl is $C_1$–$C_3$, particularly $C_2$, and especially methyl; and preferred alkyl is unsubstituted.

As used herein, "alkanyl" means a saturated hydrocarbon substituent, straight or branched chain, unsubstituted or substituted.

As used herein, "alkenyl" means a hydrocarbon substituent with one double bond, straight or branched chain, unsubstituted or substituted.

As used herein, "alkylthio" means a substituent having the structure Q—S—, where Q is alkyl.

As used herein, "alkoxy" means a substituent having the structure Q—O—, where Q is alkyl.

As used herein, "amide" means a substituent having the structure $NH_2$—CO—, where one or both hydrogens on the nitrogen can be substituted with alkyl.

As used herein, "amido" means a substituent having the structure H—CO—NH—, where the hydrogen, on the carbon can be substituted with alkyl.

As used herein, "halo" means fluoro, chloro, bromo and iodo.

As used herein, "sulfoxide" means a substituent having the structure HSO—, where the hydrogen can be substituted with alkyl.

As used herein, "sulfonyl" means a substituent having the structure $HSO_2$—, where the hydrogen can be substituted with alkyl.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, incorporated by reference herein. Preferred cationic salts include the alkali metal salts (such as sodium and potassium), alkaline earth metal salts (such as magnesium and calcium) and organic salts. Preferred anionic salts include halides, sulfonates, carboxylates, phosphates, and the like. Clearly contemplated in such salts are addition salts that may provide an optical center, where once there was none. For example, a chiral tartrate salt may be prepared from the compounds of the invention, and this definition includes such chiral salts.

The compounds of the invention are sufficiently basic to form acid-addition salts. The compounds are useful both in the free base form and the form of acid-addition salts, and both forms are within the purview of the invention. The acid-addition salts are in some cases a more convenient form for use. In practice, the use of the salt form inherently amounts to the use of the base form of the active. Acids used to prepare acid-addition salts include preferably those which produce, when combined with the free base, medicinally acceptable salts. These salts have anions that are relatively innocuous to the animal organism, such as a mammal, in medicinal doses of the salts so that the beneficial property inherent in the free base are not vitiated by any side effects ascribable to the acid's anions.

Examples of appropriate acid-addition salts include, but at not limited to hydrochloride, hydrobromide, hydroiodiode, sulfate, hydrogensulfate, acetate, trifluoroacetate, nitrate, maleate, citrate, fumarate, formate, stearate, succinate, mallate, malonate, adipate, glutarate, lactate, propionate, butyrate, tartrate, methanesulfonate, trifluoromethanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds are prepared by several methods. For example the free base can be dissolved in an aqueous alcohol solution containing the appropriate acid and the salt is isolated by evaporation of the solution. Alternatively, they may be prepared by reacting the free base with an acid in an organic solvent so that the salt separates directly. Where separation of the salt is difficult, it can be precipitated with a second organic solvent, or can be obtained by concentration of the solution.

Although medicinally acceptable salts of the basic compounds are preferred, all acid-addition salts are within the scope of the present invention. All acid-addition salts are useful as sources of the free base form, even if the particular salt per se is desired only as an intermediate product. For example, when the salt is formed only for purposes of purification or identification, or when it is used as an intermediate in preparing a medicinally acceptable salt by 35 ion exchange procedures, these salts are clearly contemplated to be a part of this invention.

"Biohydrolyzable amide" refers to an amide of the compound of the invention that is readily converted in vivo by a mammal subject to yield an active compound of the invention.

A "biohydrolyzable ester" refers to an ester of the compound of the invention that is readily converted by a mammal subject to yield an active compound of the invention.

"Optical isomer", "stereoisomer", "enantiomer," "diastereomer," as referred to herein have the standard art recognized meanings (Cf., *Hawleys Condensed Chemical Dictionary*, 11th Ed.). Of course, an addition salt may provide an optical center, where once there was none. For example, a chiral tartrate salt may be prepared from the compounds of the invention, and this definition includes such chiral salts. It will be apparent to the skilled artisan that disclosure of the racemic mixture alone discloses any enantiomers therein. Thus by one disclosure, more than one compound is taught.

As used herein "animal" includes "mammals" which includes "humans".

The skilled artisan will appreciate that tautomeric forms will exist in certain compounds of the invention. For example, when the 2-iminoimidazolidinyl form of the molecule is shown, it is understood to include the 2-imidazolinylamino form of that molecule although not specifically depicted. Thus, in this description the disclosure of one tautomeric form discloses each and all of the tautomers.

The illustration by scheme of example of specific protected forms and other derivatives of the Formula (I) compounds is not intended to be limiting. The application of other useful protecting groups, salt forms, etc. is within the ability of the skilled artisan.

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyacetyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

Compounds

The subject invention involves novel compounds having the following structure:

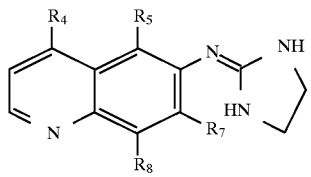

In the above structure, $R_4$ is selected from hydrogen; unsubstituted alkanyl or alkenyl having from 1 to about 3 carbon atoms; methyl monosubstituted with hydroxy, thiol or amino; unsubstituted alkylthio or alkoxy having from 1 to about 3 carbon atoms; amino; halo; unsubstituted amide; amido, unsubstituted or substituted with alkanyl or alkenyl having from 1 to about 3 carbon atoms; unsubstituted sulfoxide; unsubstituted sulfonyl; and cyano. $R_4$ which is alkanyl or alkenyl is preferably unsubstituted. $R_4$ is also preferably alkanyl, more preferably methyl or ethyl, most preferably methyl. $R_4$ which is alkylthio or alkoxy is preferably saturated, also preferably $C_1$ or $C_2$, more preferably methylthio or methoxy. $R_4$ which is halo is preferably fluoro, chloro or bromo, more preferably chloro, or especially fluoro. $R_4$ which is amido is preferably unsubstituted or substituted with methyl or ethyl. $R_4$ is also preferably cyano.

In the above structure, $R_5$ is unsubstituted alkanyl or alkenyl having from 1 to about 3 carbon atoms; cycloalkanyl or cycloalkenyl. $R_5$ is preferably alkanyl. $R_5$ is more preferably methyl or ethyl, most preferably methyl.

In the above structure, $R_7$ is selected from hydrogen; unsubstituted alkanyl or alkenyl having from 1 to about 3 carbon atoms; hydroxy, thiol or amino; halo and cyano. $R_7$ which is alkanyl or alkenyl is preferably unsubstituted. $R_7$ is also preferably alkanyl, more preferably methyl or ethyl, most preferably methyl. $R_7$ which is halo is preferably fluoro, chloro or bromo, more preferably chloro, or especially fluoro.

In the above structure, $R_8$ is selected from hydrogen unsubstituted alkanyl or alkenyl having from 1 to about 3 carbon atoms; unsubstituted alkylthio or alkoxy having from 1 to about 3 carbon atoms; hydroxy; thiol; and halo. $R_8$ is preferably alkanyl, more preferably methyl or ethyl, most preferably methyl. $R_8$ which is alkylthio or alkoxy is preferably saturated, also preferably $C_1$ or $C_2$, more preferably methylthio or methoxy. $R_8$ which is halo is preferably chloro or bromo, more preferably chloro.

Preferred compounds of the subject invention are compounds having the following structure:

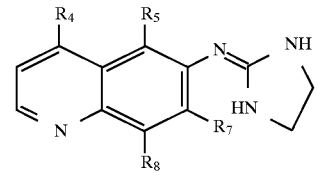

where $R_4$, $R_5$, $R_7$ and $R_8$ are as indicated in the following table:

| Compound No. | $R_4$ | $R_5$ | $R_7$ | $R_8$ |
|---|---|---|---|---|
| 1 | H | $CH_3$ | H | $CH_3$ |
| 2 | $CH_3$ | $CH_3$ | H | $CH_3$ |
| 3 | $OCH_3$ | $CH_3$ | H | $CH_3$ |
| 4 | CN | $CH_3$ | H | $CH_3$ |
| 5 | H | $CH_3$ | $CH_3$ | H |
| 6 | Cl | $CH_3$ | H | $CH_3$ |
| 7 | F | $CH_3$ | H | $CH_3$ |
| 8 | H | $CH_3$ | H | $OCH_3$ |
| 9 | H | $CH_3$ | H | Cl |

The compounds of the subject invention are synthesized using the following general procedures:

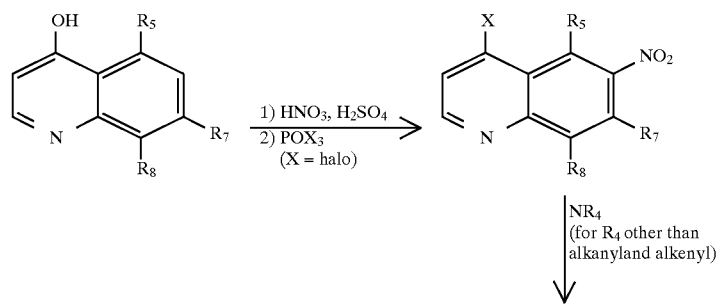

-continued

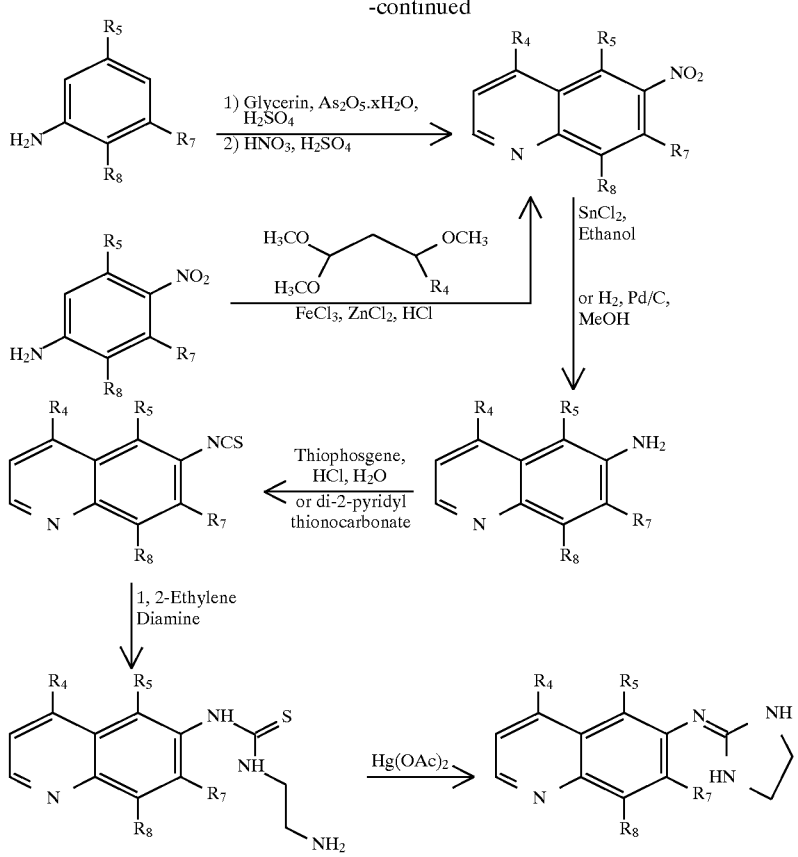

In the above scheme, where $R_8$ is alkoxy or alkylthio, the corresponding hydroxy or thiol compounds are derived from the final compounds by using a standard dealkylating procedure (Bhatt, et al., "Cleavage of Ethers", *Synthesis*, 1983, pp. 249–281). In the above scheme, when $R_4$ =cyano, the cyano moiety can be converted to substituted methyl or amide by standard functional group conversions.

It will be apparent to the skilled artisan that the reactions illustrated above are known reactions. Furthermore, it is within the purview of the skilled artisan to vary these reactions to prepare compounds within the scope of the claims.

The starting materials used in preparing the compounds of the invention are known, made by known methods, or are commercially available as a starting material.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March, *Advanced Organic Chemistry* (Wiley), Carey and Sundberg, *Advanced Organic Chemistry* (2 vol.) and Trost and Fleming *Comprehensive Organic Synthesis* (6 vol.).

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations are found, for example, in T. Greene, *Protecting Groups in Organic Synthesis*.

The following non-limiting examples provide details for the syntheses of compounds of 6-(2-imidazolinylamino) quinoline the subject invention.

EXAMPLE 1

Synthesis of 5,8-dimethyl-6-(2-imidazolinylamino) quinoline:

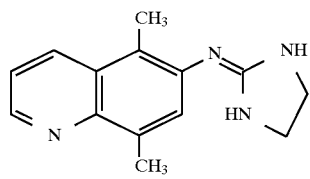

A. 5,8-Dimethylquinoline. To a mixture of 2,5-dimethylaniline (20.73 g), glycerin (54.81 g) and arsenic pentoxide hydrate ($As_2O_5 \cdot xH_2O$) (Aldrich, 54% As, 35.06 g) under argon and in a 1L 3-neck round bottom flask equipped with a mechanical stirrer is carefully added sulfuric acid (51.6 g). The resulting hot solution is then heated at 140°–150° C. for 4 hours. The reaction mixture is then cooled to room temperature and slowly basified to pH=10 by the addition of ammonium hydroxide solution (28–30%). After a period of about 10 minutes the basic solution is acidified to pH=5 by the addition of glacial acetic acid and extracted with methylene chloride (CH$_2$Cl$_2$) (3×500 mL). The organic layer is then washed with water (2×500 mL) and brine (2×500 mL), dried over magnesium sulfate (MgSO$_4$), filtered, and rotary evaporated to yield crude quinoline (31 g) which is flash chromatographed on silica gel eluting with 10% ethyl acetate/hexanes. Compound-containing fractions are combined and rotary evaporated to yield 5,8-dimethylquinoline.

B. 5,8-Dimethyl-6-nitroquinoline. 5,8-dimethylquinoline (1.25 g), in a 250 mL round bottom flask is cooled to 0° C. in an ice/sodium chloride bath under argon. Concentrated sulfuric acid (50 mL) is added slowly via addition funnel so that the internal temperature does not exceed 5° C. The solution is allowed to stir a few minutes then cooled to -15° C. in an ethylene glycol/dry ice bath. Nitric acid (1.7 mL, 69–71%) in sulfuric acid (50 mL) is added dropwise (via syringe) at such a rate that the reaction temperature does not exceed −3° C. After 10 minutes, the reaction is poured into a beaker of ice and basified slowly to pH=10 by the addition of ammonium hydroxide solution (28–30%). The product is extracted with ethyl acetate (3×500 mL). The organic layer is dried over magnesium sulfate, filtered, and rotary evaporated to yield crude product (2.6 g) which is flash chromatographed on silica gel eluting with 15% ethyl acetate/hexanes. Compound-containing fractions are combined and rotary evaporated to yield 5,8-dimethyl-6-nitroquinoline.

C. 5,8-Dimethyl-6-aminoguinoline. To a solution of 5,8-dimethyl-6-nitroquinoline (1.41 g) in ethanol (17.4 mL) under argon is added iron (Fe) (1.21 g) and glacial acetic acid (2.56 g). The mixture is refluxed for two hours. More Fe (1.23 g) and glacial acetic acid (2.49 g) are added to the reaction, which is allowed to reflux for an additional hour. The reaction is poured into a beaker of ice and adjusted to pH 10 by careful addition of a saturated solution of potassium carbonate. The product is extracted with methylene chloride and the organic layer is dried over sodium sulfate, filtered, and rotary evaporated to give 5,8-dimethyl-6-aminoquinoline.

D. 5,8-Dimethyl-6-isothiocyanotoquinoline. To a solution of 5,8-dimethyl-6-aminoquinoline (0.85 g) in 0.1N HCl (52 mL) is added thiophosgene (0.4 mL) dropwise. The reaction is stirred for 10 minutes, by which time a yellow precipitate has formed. 1 N Sodium hydroxide (NaOH) (52 mL) is added to the reaction and a white precipitate forms immediately. The reaction mixture is allowed to stir for 10 minutes, after which time the product is extracted with methylene chloride (3×100 mL). The organic layer is evaporated to a small volume and the residue filtered through a bed of silica gel, which is eluted with 25% ethyl acetate/hexanes. The filtrate is evaporated to yield 5,8-dimethyl-6-isothiocyantoquinoline.

E. 6[-N'-(2-Aminoethyl)thioureido]-5.8-dimethylquinoline. To a solution of ethylene diamine (2.00 mL) in toluene (21 mL) under argon is added dropwise a solution of 5,8-dimethyl-6-isothiocyanatoquinoline (0.88 g) in toluene (21 mL). A white precipitate forms during the addition. The toluene is evaporated and the yellow-white solid dried under a vacuum for 20 minutes to yield 6-[N'-(2-aminoethyl) thioureido]-5,8-dimethylquinoline.

F. 5,8-Dimethyl-6-(2-imidazolinylamino)quinoline. A mixture of 6-[N'-(2-aminoethyl)thioureido]-5,8-dimethylquinoline (1.12 g) and mercuric acetate (1.85 9) in ethanol (41 mL) is heated to reflux. As the reaction warms to reflux, the mixture turns dark brown. After a few minutes at reflux temperature, the reaction becomes black. The cooled reaction mixture is filtered through a bed of Celite, which is washed with ethanol. The filtrate is rotary evaporated and the residue taken up in water and basified to pH=10 with a saturated solution of potassium carbonate. The product is extracted with chloroform (3×250 mL). The organic layer is evaporated to a small volume which is then filtered through a bed of silica gel to remove residual mercury salts. The bed is washed with copious amounts of methanol and the filtrate is rotary evaporated to yield 1.3 g of crude product. A solution (10 mL) of this crude material in methylene chloride is filtered through another bed of silica gel to remove baseline material, washing the bed with 20% sat. methanolic NH$_3$/chloroform and rotary evaporated to a crude material which is suspended in boiling ethyl acetate and filtered hot. The filtered material is the desired 5,8-dimethyl-6-(2-imidazolinylamino)quinoline (0.51 g).

EXAMPLE 2

Synthesis of 6-(2-imidazolinylamino)-4,5,8-trimethylquinoline:

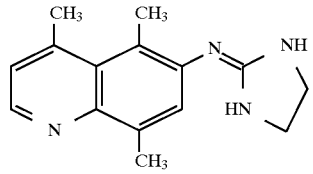

A. 6-Nitro-4,5,8-trimethylquinoline. A mixture of 2,5-dimethyl-4-nitroaniline (0.96 g), ferric chloride hexahydrate (2.50 g), zinc chloride (0.094 g), concentrated hydrochloric acid (0.481 mL), and ethanol (8 mL) is heated to 60° C. 1,3,3-trimethoxybutane (0.73 mL) is added dropwise while the reaction mixture is kept at 60° C. The reaction mixture is heated at reflux overnight and cooled to room temperature. A solution of 10% aqueous sodium hydroxide is added, and the mixture is extracted three times with methylene chloride. The combined organic layers are dried over sodium sulfate, filtered and evaporated to afford a crude product. The crude product is purified by flash chromatography using 25% ethyl acetate in hexanes as eluent, providing 6-nitro-4,5,8-trimethylquinoline.

B. 6-Amino-4,5,8-trimethylquinoline. A mixture of 6-nitro-4,5,8-trimethylquinoline (0.60 g), stannous chloride dihydrate (3.13 g), and ethanol (40 mL) is heated for 3 hours at 60–65° C. and then cooled to room temperature. 10% Aqueous sodium hydroxide (24 mL) and water (48 mL) are added, and the mixture is extracted three times with chloroform. The combined organic layers are washed with saturated sodium bicarbonate solution, dried over sodium sulfate, filtered and evaporated to afford a crude product. The crude product is purified by flash chromatography using 25% ethyl acetate in hexanes as eluent, providing 6-amino-4,5,8-trimethylquinoline.

C. 6-lsothiocyanato-4,5,8-trimethylquinoline. A mixture of 6-amino-4,5,8-trimethylquinoline (0.37 g), di-2-pyridyl thionocarbonate (0.494 g) (DPT), dimethylaminopyridine (0.052 g) and methylene chloride (4 mL) is stirred at room temperature for 2 hours. An additional 100 mg of DPT is added, and stirring is continued for one hour. Another 100 mg portion of DPT is added, and the reaction is stirred at room temperature for one more hour. The mixture is concentrated by evaporation and purified by chromatography through a short column consisting of layers of sand/flash silica gel/sand, using 20% ethyl acetate in hexanes as the eluting solvent, providing 6-isothiocyanato-4,5,8-trimethylquinoline.

D. 6-[N'-(2-Aminoethyl)thioureido]-4,5,8-trimethylquinoline To a solution of ethylene diamine (0.586 mL) in 2.5 mL of toluene is slowly added a solution of 6-isothiocyanato-4,5,8-trimethylquinoline (0.40 g) in toluene (10 mL). The reaction mixture is stirred at room temperature for 2 hours and then placed in a refrigerator overnight. The solid which forms is filtered, washed well with toluene, and dried, providing 6-[N'-(2-aminoethyl)thioureido]-4,5,8-trimethylquinoline.

E. 6-(2-Imidazolinylamino)-4 5,8-trimethylquinoline. A mixture of 6-[N'-(2-aminoethyl)thioureido]-4,5,8-trimethylquinoline (0.461 g), mercuric acetate (0.602 g), and methanol (20 mL) is stirred at room temperature for 4 hours. The reaction mixture is filtered though Celite, and the Celite is washed with methanol. The filtrate is evaporated. The crude product is purified by flash chromatography, eluting with a 20% methanol in methylene chloride solution, containing 1% ammonium hydroxide, providing 6-(2-imidazolinylamino)-4,5,8-trimethylquinoline.

EXAMPLE 3

Synthesis of 5,8-dimethyl-6-(2-imidazolinylamino)-4-methoxyquinoline:

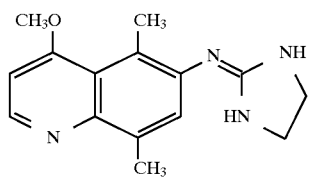

A. 5,8-Dimethyl-6-nitro-4-quinolone. In a flask is placed 5,8-dimethyl-4-quinolone (5.18 g, 29.9 mmol) (prepared according to Burckhalter, et al., *J. Am. Chem. Soc.*, Vol. 70 (1948), p. 1363) with sulfuric acid (30 mL). After stirring for 10 minutes, the flask is cooled in ice and concentrated nitric acid (1.90 mL, 30.2 mmol) is added dropwise. After the addition is completed, the mixture is stirred for 15 minutes in ice. The mixture is then poured onto crushed ice and allowed to warm to room temperature. The gray solid is filtered and washed with water. The solid is recrystallized from hot methanol to give 5,8-dimethyl-6-nitro-4-quinolone.

B. 4-Chloro-5,8-dimethyl-6-nitroquinoline. In a flask is placed 5,8-dimethyl-6-nitro-4-quinolone (3.01 g, 13.8 mmol) with phosphorus oxychloride (41.3 g, 268 mmol). The mixture is refluxed under argon with stirring for 3 hours. After cooling to room temperature the mixture is poured on crushed ice, and concentrated ammonium hydroxide (100 mL) is added. Extraction with chloroform (2×200 mL), drying over potassium carbonate, filtration and solvent removal by rotary evaporation gives 4-chloro-5,8-dimethyl-6-nitroquinoline.

C. 5,8-Dimethyl-4-methoxy-6-nitroquinoline. In a flask is placed 4-chloro-5,8-dimethyl-6-nitroquinoline (1.52 g, 5.4 mmol) with sodium methoxide (2.27 g, 4.2 mmol) and methanol (25 mL). The mixture is refluxed under argon with stirring for 21 hours, diluted with water (100 mL) and methanol (50 mL) and extracted with methylene chloride (2×200 mL). The organic layer is dried over potassium carbonate, filtered and evaporated. The product is purified by flash chromatography (7/3 hexanes/ethyl acetate), yielding 5,8-dimethyl-4-methoxy-6-nitroquinoline.

D. 4-Amino-5,8-dimethyl-4-methoxyquinoline. In a flask is placed 5,8-dimethyl-4-methoxy-6-nitroquinoline (1.16 g, 5.0 mmol) with stannous chloride dihydrate (5.64 g, 25 mmol) and ethanol (50 mL). The mixture is refluxed for 1 hour, diluted with water (100 mL) and concentrated ammonium hydroxide (30 mL), and extracted with chloroform (2×200 mL). The organic portion is dried over potassium carbonate, filtered and the solvents removed by rotary evaporation, yielding 4-amino-5,8-dimethyl-4-methoxyquinoline.

E. 5,8-Dimethyl-6-isothiocyanato-4-methoxyquinoline. A solution of 6-amino-5,8-dimethyl-4-methoxyquinoline (987 mg, 4.9 mmol), di-2-pyridyl-thionocarbonate (1.74 g, 7.5 mmol), and methylene chloride (70 mL) is stirred at room temperature for 2 hours. The solvent is removed by rotary evaporation and the product is purified by flash chromatography (8/2 hexanes/ethyl acetate) to give 5,8-dimethyl6-isothiocyanato-4-methoxyquinoline.

F. 5,8-Dimethyl-4-methoxy-6-[N'-(2-aminoethyl)thioureido]quinoline. To ethylenediamine (2.25 g, 37 mmol) is added dropwise a solution of 5,8-dimethyl-6-isothiocyanato-4-methoxyquinoline (501 mg, 2.1 mmol) dissolved in methylene chloride (20 mL). The mixture is stirred at room temperature overnight. The resulting solid is removed by filtration and washed with a small volume of methylene chloride. The remaining solid is dried under a vacuum for several hours, providing 5,8-dimethyl-4-methoxy-6-[N'-(2-aminoethyl)thioureido]quinoline.

G. 5,8-Dimethyl-6-(2-imidazolinylamino)-4-methoxyquinoline. A mixture of 5,8-dimethyl-4-methoxy-6-[N'-(2-aminoethyl)thioureido]quinoline (493 mg, 1.6 mmol) and mercuric acetate (537 mg, 1.7 mmol) in methanol (60 mL), is stirred at room temperature for 2 hours, and then filtered through Celite. The filtrate is added to 10% aqueous potassium carbonate (100 mL), extracted with chloroform (3×200 mL). The organic layer is dried over potassium carbonate, filtered and evaporated to a residue which is purified by flash chromatography (9/1 chloroform/methanol saturated with ammonia) providing 5,8-dimethyl-4-methoxy6-(2-imidazolinylamino)quinoline.

EXAMPLE 4

Synthesis of 4-cyano-5,8-dimethyl-6-(2-imidazolinylamino)quinoline:

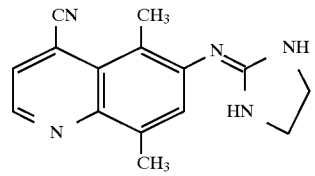

A. 4-Bromo-5,8-dimethyl-6-nitroquinoline. A mixture of 5,8-dimethyl-6-nitro-4-quinolone (7.12 g, 32.7 mmol), phosphorus oxybromide (7.47 g, 26.12 mmol), pyridine (5.3 mL), and toluene (90 mL) is heated at 90° C. for 6 hours. The mixture is filtered hot, and the solid is washed with water and methylene chloride. The filtate is extracted with methylene chloride (3×100 mL), and the combined organic layers are dried (sodium sulfate) and evaporated to afford 4-bromo-5,8-dimethyl-6-nitroquinoline.

B. 4-Cyano-5,8-dimethyl-6-nitroquinoline. A mixture of 4-bromo-5,8-dimethyl-6-nitroquinoline (3.87 g, 13.77 mmol), cuprous cyanide (3.67 g, 41.31 mmol) and dimethylformamide (70 mL) is stirred at room temperature for 30 minutes and then heated to 155° C. and stirred at this temperature for 1 hour. Water is added, and the reaction mixture is filtered. The precipitate is washed with water and methylene chloride. The filtrate is extracted with methylene chloride (3×125 mL), and the combined organic layers are dried (sodium sulfate) and evaporated. Purification by chromatography through a short column consisting of layers of sand/flash silica gel/sand, using chloroform as eluent, provides 4-cyano-5,8-dimethyl-6-nitroquinoline.

C. 6-Amino-4-cyano-5,8-dimethylquinoline. A mixture of 4-cyano-5,8-dimethyl-6-nitroquinoline (2.54 g, 11.2 mmol), stannous chloride dihydrate (12.6 g, 55.9 mmol) and ethanol (200 mL) is heated at 60° C. for 1.5 hours. The reaction is cooled to room temperature, and water (60 mL) is added. The mixture is basified with 10% aqueous sodium hydroxide solution (70 mL) and subsequently extracted with methylene chloride (3×150 mL). Drying (sodium sulfate) and evaporation provides 6-amino-4-cyano-5,8-dimethylquinoline.

D. 4-Cyano-5,8-dimethyl-6-isothiocyanatoquinoline. A mixture of 6-amino-4-cyano-5,8-dimethylquinoline (2.0 g, 10.15 mmol), di-2-pyridyl thionocarbonate (2.52 g, 10.86 mmol), dimethylaminopyridine (0.266 g, 2.18 mmol) and methylene chloride (62 mL) is stirred at room temperature for 1.5 hours. Evaporation affords a residue which is purified by chromatography through a short column consisting of layers of sand/flash silica gel/sand, using methylene chloride as eluent, to give 4-cyano-5,8-dimethyl-6-isothiocyanatoquinoline.

6-[N'-(2-Aminoethyl)thioureido]-4-cyano-5,8-dimethylquinoline. To a solution of ethylenediamine (2.93 mL) in toluene (30 mL) is slowly added a solution of 4-cyano-5,8-dimethyl-6-isothiocyanatoquinoline (2.1 g, 8.78 mmol) in toluene (100 mL). The reaction mixture is stirred at room temperature overnight. The solid which forms is filtered, washed well with toluene, and dried to afford 6-[N'-(2-aminoethyl)thioureido]-4-cyano-5,8-dimethylquinoline.

4-Cyano-5,8-dimethyl-6-(2-imidazolinylamino) quinoline. A mixture of 6-[N'-(2-aminoethyl)thioureido]4-cyano-5,8-dimethylquinoline (2.49 g, 8.32 mmol), mercuric acetate (2.81 g, 8.82 mmol) and methanol (100 mL) is stirred at room temperature for 2 hours, resulting in a black suspension. The suspension is filtered through a bed of silica gel and Celite, and the bed is washed well with methanol. The filtrate is evaporated to dryness. Purification is accomplished by chromatography through a short column consisting of layers of sand/flash silica gel/sand, using methylene chloride/methanol/ammonium hydroxide (85/15/2) as eluent. This provides 4-cyano-5,8-dimethyl-6-(2-imidazolinylamino)quinoline, as a partial acetatic acid salt.

EXAMPLE 5

Synthesis of 5,7-dimethyl-6-(2-imidazolinylamino) quinoline

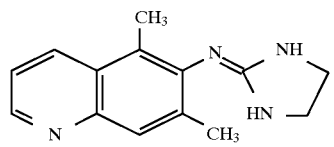

A. 5,7-Dimethyl-6-nitroquinoline. A solution of 1,1,3-trimethoxypropane (560 mg, 4.2 mmol) in 4 mL of ethanol is added dropwise over 2 hours (syringe pump) to a heated (60° C.) mixture of 3,5-dimethyl-4-nitroaniline (500 mg, 3 mmol), ferric chloride hexahydrate (1.06 g, 3.9 mmol) and zinc chloride (45 mg, 0.33 mmol) in 70 mL of ethanol and 3 mL of 1N hydrochloric acid. The resulting mixture is heated to reflux for 4 hours, then stirred at room temperature for 10 hours. The mixture is basified with concentrated ammonium hydroxide. The precipitate is filtered and washed with ethyl acetate. The filtrate is extracted with ethyl acetate and the combined organic layers are dried over magnesium sulfate and rotary evaporated. The residue is purified by flash chromatography on silica gel, eluting with 50% ethyl acetate/hexanes to give 5,7-dimethyl-6-nitroquinoline as an ochre solid.

B. 6-Amino-5,7-dimethylquinoline. A mixture of 5,7-dimethyl-6-nitroquinoline (200 mg, 0.99 mmol) and 10% palladium-on-carbon (50 mg) in 30 mL of methanol is stirred at room temperature under hydrogen at atmospheric pressure for 15 hours. The mixture is filtered on Celite with a methanol wash of the solids. The filtrate is rotary evaporated and the residue is purified by flash chromatography on silica gel, eluting with 50% ethyl acetate/hexanes to provide 6-amino-5,7-dimethylquinoline as a yellow oil.

C. 5,7-Dimethyl-6-isothiocyanatoquinoline. To a solution of di-2-pyridyl thionocarbonate (215 mg, 0.93 mmol) and 4-dimethylaminopyridine (10 mg) in 30 mL of methylene chloride is added dropwise a solution of 6-amino-5,7-dimethylquinoline (123 mg, 0.71 mmol) in 15 mL of methylene chloride. The mixture is stirred for 5 hours at room temperature then rotary evaporated. The residue is purified by flash chromatography on silica gel, eluting with 25% ethyl acetate/hexanes to provide 5,7-dimethyl-6-quinolinyl isothiocyanate as a pale yellow solid.

D. 5,7-Dimethyl-6-(2-imidazolinylamino)quinoline. A solution of 5,7-dimethyl-6-isothiocyanatoquinoline (120 mg, 0.56 mmol) in 20 mL of methylene chloride is added dropwise to ethylenediamine (168 mg, 2.8 mmol) in solution in 30 mL of methylene chloride. The mixture is stirred for 2 hours at room temperature then rotary evaporated. The residue is dissolved in 30 mL of methanol and treated with mercuric acetate (214 mg, 0.67 mmol) at room temperature for 15 hours. The resulting black mixture is filtered on Celite with a methanol wash of the solids, and the filtrate is rotary evaporated. The residue is purified by flash chromatography on a short pad of silica gel, eluting with a 16/16/1 mixture of ethyl acetate/methanol/ammonium hydroxide to provide 5,7-dimethyl-6-(2-imidazolinylamino)quinoline, as a diacetic acid salt.

Alternative Imidazolinylamine Formation from Aryl Amines

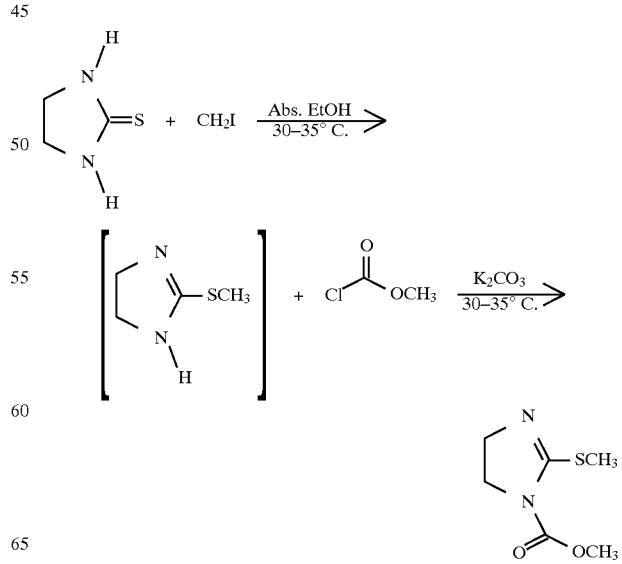

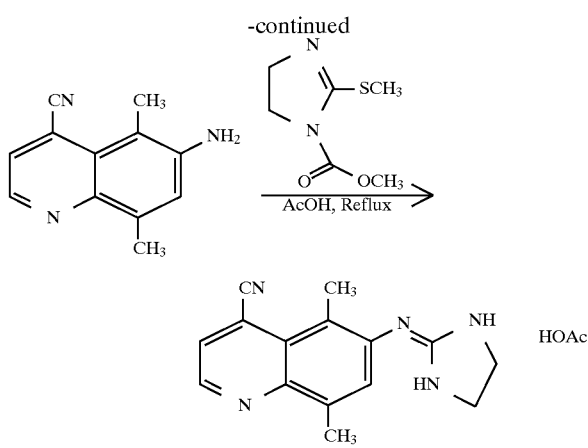

A. 2-Methylthio-2-imidazoline. 2-Imidazolidinethione (5.0 g) is added to absolute ethanol (40 mL) while stirring. Methyl iodide (4.3 ml) is rapidly added. The reaction mixture is warmed to 30°–35° C. for 45 minutes. This solution is used directly in the next reaction.

B. N-Carbomethoxy-2-thiomethyl-2-imidazoline. Potassium carbonate (10.1 g) is added to the mixture in (A) above, followed by addition of methyl chloroformate (4.2 mL) while stirring. After 45 minutes, the reaction mixture is heated to 55° C. and the insoluble salts are filtered off. These salts are washed with 10 mL of absolute ethanol. The filtrate (and ethanol wash) is cooled to −20° C. and the recrystallized product is isolated on a Buchner funnel. The product is washed with 10 mL cold (−20° C.) absolute ethanol. The product is dried overnight under vacuum at room temperature, yielding N-carbomethoxy-2-thiomethyl-2-imidazoline.

C. 4-Cyano-5,8-dimethyl-6-(2-imidazolinylamino) quinoline. The N-carbomethoxy-2-thiomethyl-2-imidazoline is combined with the amine (4C) of Example 4 in 10% acetic acid in ehtanol and heated to reflux. After the starting amine is consumed, the mixture is decolorized with carbon. The mixture is cooled, filtered and rotary evaporated. Upon recrystallization and drying, the compound (4F) of Example 4 is obtained as an acetic acid salt.

Compositions

Another aspect of this invention is compositions which comprise a safe and effective amount of a subject compound, or a pharmaceutically-acceptable salt thereof, and a pharmaceutically-acceptable carrier.

As used herein, "safe and effective amount" means an amount of the subject compound sufficient to significantly induce a positive modification in the condition to be treated, but low enough to avoid serious side effects (at a reasonable benefit/risk ratio), within the scope of sound medical judgment. A safe and effective amount of the subject compound will vary with the age and physical condition of the patient being treated, the severity of the condition, the duration of the treatment, the nature of concurrent therapy, the particular pharmaceutically-acceptable carrier utilized, and like factors within the knowledge and expertise of the attending physician.

Preparing a dosage form is within the purview of the skilled artisan. Examples are provided for the skilled artisan, but are non-limiting, and it is contemplated that the skilled artisan can prepare variations of the compositions claimed.

Compositions of this invention preferably comprise from about 0.0001% to about 99% by weight of the subject compound, more preferably from about 0.01% to about 90% of the compound of the invention. Depending upon the route of administration and attendant bioavailability, solubility or dissolution characteristics of the dosage form, the dosage form has preferably from about 10% to about 50%, also preferably from about 5% to about 10%, also preferably from about 1% to about 5%, and also preferably from about 0.01% to about 1% of the subject compound. The frequency of dosing of the subject compound is dependent upon the pharmacokinetic properties of each specific agent (for example, biological half-life) and can be determined by the skilled artisan.

In addition to the subject compound, the compositions of this invention contain a pharmaceutically-acceptable carrier. The term "pharmaceutically-acceptable carrier", as used herein, means one or more compatible solid or liquid filler diluents or encapsulating substances which are suitable for administration to a mammal. The term "compatible", as used herein, means that the components of the composition are capable of being commingled with the subject compound, and with each other, in a manner such that there is no interaction which would substantially reduce the pharmaceutical efficacy of the composition under ordinary use situations. Preferably when liquid dose forms are used, the compounds of the invention are soluble in the components of the composition. Pharmaceutically-acceptable carriers must, of course, be of sufficiently high purity and sufficiently low toxicity to render them suitable for administration to the mammal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the subject compound is basically determined by the way the compound is to be administered. If the subject compound is to be injected, the preferred pharmaceutically-acceptable carrier is sterile, physiological saline, with a blood-compatible suspending agent, the pH of which has been adjusted to about 7.4.

If the preferred mode of administering the subject compound is perorally, the preferred unit dosage form is therefore tablets, capsules, lozenges, chewable tablets, and the like. Such unit dosage forms comprise a safe and effective amount of the subject compound, which is preferably from about 0.01 mg to about 350 mg, more preferably from about 0.1 mg to about 35 mg, based on a 70 kg person. The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of this invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.001% to about 5% of the subject compound, more preferably from about 0.01% to about 0.5%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Compositions can also be used to deliver the compound to the site where activity is desired: intranasal doses for nasal decongestion, inhalants for asthma, and eye drops, gels and creams for ocular disorders.

Preferred compositions of this invention include solutions or emulsions, preferably aqueous solutions or emulsions comprising a safe and effective amount of a subject compound intended for topical intranasal administration. Such compositions preferably comprise from about 0.001% to about 25% of a subject compound, more preferably from about 0.01% to about 10%. Similar compositions are preferred for systemic delivery of subject compounds by the intranasal route. Compositions intended to deliver the compound systemically by intranasal dosing preferably comprise similar amounts of a subject compound as are determined to be safe and effective by peroral or parenteral administration. Such compositions used for intranasal dosing also typically include safe and effective amounts of preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfate and others; aromatic agents; viscosity adjustors, such as polymers, including cellulose and derivatives thereof, and polyvinyl alcohol and acids and bases to adjust the pH of these aqueous compositions as needed. The compositions may also comprise local anesthetics or other actives. These compositions can be used as sprays, mists, drops, and the like.

Other preferred compositions of this invention include aqueous solutions, suspensions, and dry powders comprising a safe and effective amount of a subject compound intended for atomization and inhalation administration. Such compositions preferably comprise from about 0.1% to about 50% of a subject compound, more preferably from about 1% to about 20%; of course, the amount can be altered to fit the circumstance of the patient contemplated and the package. Such compositions are typically contained in a container with attached atomizing means. Such compositions also typically include propellants such as chlorofluorocarbons 12/11 and 12/114, and more environmentally friendly fluorocarbons, or other nontoxic volatiles; solvents such as water, glycerol and ethanol, these include cosolvents as needed to solvate or suspend the active; stabilizers such as ascorbic acid, sodium metabisulfite; preservatives such as cetylpyridinium chloride and benzalkonium chloride; tonicity adjustors such as sodium chloride; buffers; and flavoring agents such as sodium saccharin. Such compositions are useful for treating respiratory disorders, such as asthma and the like.

Other preferred compositions of this invention include aqueous solutions comprising a safe and effective amount of a subject compound intended for topical intraocular administration. Such compositions preferably comprise from about 0.0001% to about 5% of a subject compound, more preferably from about 0.01% to about 0.5%. Such compositions also typically include one or more of preservatives, such as benzalkonium chloride, thimerosal, phenylmercuric acetate; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases may be used to adjust the pH of these formulations as needed.

Other preferred compositions of this invention useful for peroral administration include solids, such as tablets and capsules, and liquids, such as solutions, suspensions and emulsions (preferably in soft gelatin capsules), comprising a safe and effective amount of a subject compound. Such compositions preferably comprise from about 0.01 mg to about 350 mg per dose, more preferably from about 0.1 mg to about 35 mg per dose. Such compositions can be coated by conventional methods, typically with pH or time-dependent coatings, such that the subject compound is released in the gastrointestinal tract at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit® coatings, waxes and shellac.

Any of the compositions of this invention may optionally include other drug actives. Non-limiting examples of drug actives which may be incorporated in these compositions, include:

Antihistamines, including:

Hydroxyzine, preferably at a dosage range of from about 25 to about 400 mg; Doxylamine, preferably at a dosage range of from about 3 to about 75 mg; Pyrilamine, preferably at a dosage range of from about 6.25 to about 200 mg; Chlorpheniramine, preferably at a dosage range of from about 1 to about 24 mg; Phenindamine, preferably at a dosage range of from about 6.25 to about 150 mg; Dexchlorpheniramine, preferably at a dosage range of from about 0.5 to about 12 mg; Dexbrompheniramine, preferably at a dosage range of from about 0.5 to about 12 mg; Clemastine, preferably at a dosage range of from about 1 to about 9 mg; Diphenhydramine, preferably at a dosage range of from about 6.25 to about 300 mg; Azelastine, preferably at a dosage range of from about 140 to about 1,680 μg (when dosed intranasally); 1 to about 8 mg (when dosed orally); Acrivastine, preferably at a dosage range of from about 1 to about 24 mg; Levocarbastine (which can be dosed as an intranasal or ocular medicament), preferably at a dosage range of from about 100 to about 800 mg; Mequitazine, preferably at a dosage range of from about 5 to about 20 mg; Astemizole, preferably at a dosage range of from about 5 to about 20 mg; Ebastine, preferably at a dosage range of from about 5 to about 20 mg; Loratadine, preferably at a dosage range of from about 5 to about 40 mg; Cetirizine, preferably at a dosage range of from about 5 to about 20 mg; Terfenadine, preferably at a dosage range of from about 30 to about 480 mg; Terfenadine metabolites; Promethazine, preferably at a dosage range of from about 6.25 to about 50 mg; Dimenhydrinate, preferably at a dosage range of from about 12.5 to about 400 mg; Meclizine, preferably at a dosage range of from about 6.25 to about 50 mg; Tripelennamine, preferably at a dosage range of from about 6.25 to about 300 mg; Carbinoxamine, preferably at a dosage range of from about 0.5 to about 16 mg; Cyproheptadine, preferably at a dosage range of from about 2 to about 20 mg; Azatadine, preferably at a dosage range of from about 0.25 to about 2 mg; Brompheniramine, preferably at a dosage range of from about 1 to about 24 mg; Triprolidine, preferably at a dosage range of from about 0.25 to about 10 mg; Cyclizine, preferably at a dosage range of from about 12.5 to about 200 mg; Thonzylamine, preferably at a dosage range of from about 12.5 to about 600 mg; Pheniramine, preferably at a dosage range of from about 3 to about 75 mg; Cyclizine, preferably at a dosage range of from about 12.5 to about 200 mg and others;

Antitussives, including:

Codeine, preferably at a dosage range of from about 2.5 to about 120 mg; Hydrocodone, preferably at a dosage range of from about 2.5 to about 40 mg; Dextromethorphan, preferably at a dosage range of from about 2.5 to about 120 mg; Noscapine, preferably at a dosage range of from about 3 to about 180 mg; Benzonatate, preferably at a dosage range of from about 100 to about 600 mg; Diphenhydramine, preferably at a dosage range of from about 12.5 to about 150 mg; Chlophedianol, preferably at a dosage range of from about 12.5 to about 100 mg; Clobutinol, preferably at a dosage range of from about 20 to about 240 mg; Fominoben, preferably at a dosage range of from about 80 to about 480 mg; Glaucine; Pholcodine, preferably at a dosage range of from about 1 to about 40 mg; Zipeprol, preferably at a dosage range of from about 75 to about 300 mg; Hydromorphone, preferably at a dosage range of from about 0.5 to about 8 mg; Carbetapentane, preferably at a dosage range of from about 15 to about 240 mg; Caramiphen, preferably at a dosage range of from about 10 to about 100 mg; Levopropoxyphene, preferably at a dosage range of from about 25 to about 200 mg and others;

Antiinflammatories, Preferably Non-Steroidal Anti-inflammatories, (NSAIDS) including:

Ibuprofen, preferably at a dosage range of from about 50 to about 3,200 mg; Naproxen, preferably at a dosage range of from about 62.5 to about 1,500 mg; Sodium naproxen, preferably at a dosage range of from about 110 to about 1,650 mg; Ketoprofen, preferably at a dosage range of from about 25 to about 300 mg; Indoprofen, preferably at a dosage range of from about 25 to about 200 mg; Indomethacin, preferably at a dosage range of from about 25 to about 200 mg; Sulindac, preferably at a dosage range of from about 75 to about 400 mg; Diflunisal, preferably at a dosage range of from about 125 to about 1,500 mg; Ketorolac, preferably at a dosage range of from about 10 to about 120 mg; Piroxicam, preferably at a dosage range of from about 10 to about 40 mg; Aspirin, preferably at a dosage range of from about 80 to about 4,000 mg; Meclofenamate, preferably at a dosage range of from about 25 to about 400 mg; Benzydamine, preferably at a dosage range of from about 25 to about 200 mg; Carprofen, preferably at a dosage range of from about 75 to about 300 mg; Diclofenac, preferably at a dosage range of from about 25 to about 200 mg; Etodolac, preferably at a dosage range of from about 200 to about 1,200 mg; Fenbufen, preferably at a dosage range of from about 300 to about 900 mg; Fenoprofen, preferably at a dosage range of from about 200 to about 3,200 mg; Flurbiprofen, preferably at a dosage range of from about 50 to about 300 mg; Mefenamic acid, preferably at a dosage range of from about 250 to about 1,500 mg; Nabumetone, preferably at a dosage range of from about 250 to about 2,000 mg; Phenylbutazone, preferably at a dosage range of from about 100 to about 400 mg; Pirprofen, preferably at a dosage range of from about 100 to about 800 mg; Tolmetin, preferably at a dosage range of from about 200 to about 1,800 mg and others;

Analgesics, including:

Acetaminophen, preferably at a dosage range of from about 80 to about 4,000 mg; and others:

Expectorants/Mucolytics, including:

Guaifenesin, preferably at a dosage range of from about 50 to about 2,400 mg; N-Acetylcysteine, preferably at a dosage range of from about 100 to about 600 mg; Ambroxol, preferably at a dosage range of from about 15 to about 120 mg; Bromhexine, preferably at a dosage range of from about 4 to about 64 mg; Terpin hydrate, preferably at a dosage range of from about 100 to about 1,200 mg; Potassium iodide, preferably at a dosage range of from about 50 to about 250 mg and others;

Anticholinergics (eg., Atropinics), Preferably intranasally or orally administered anticholinergics, including: Ipratroprium (preferably intranasally), preferably at a dosage range of from about 42 to about 252 μg; Atropine sulfate (preferably oral), preferably at a dosage range of from about 10 to about 1,000 μg; Belladonna (preferably as an extract), preferably at a dosage range of from about 15 to about 45 mg equivalents; Scopolamine, preferably at a dosage range of from about 400 to about 3,200 μg; Scopolamine methobromide, preferably at a dosage range of from about 2.5 to about 20 mg; Homatropine methobromide, preferably at a dosage range of from about 2.5 to about 40 mg; Hyoscyamine (preferably oral), preferably at a dosage range of from about 125 to about 1,000 μg; Isopropramide (preferably oral), preferably at a dosage range of from about 5 to about 20 mg; Orphenadrine (preferably oral), preferably at a dosage range of from about 50 to about 400 mg; Benzalkonium chloride (preferably intranasally) preferably a 0.005 to about 0.1% solution and others;

Mast Cell Stabilizers, preferably intranasally, or orally administered mast cell stabilizers, including:

Cromalyn, preferably at a dosage range of from about 10 to about 60 mg; Nedocromil, preferably at a dosage range of from about 10 to about 60 mg; Oxatamide, preferably at a dosage range of from about 15 to about 120 mg; Ketotifen, preferably at a dosage range of from about 1 to about 4 mg; Lodoxamide, preferably at a dosage range of from about 100 to about 3,000 μg and others;

Leukotriene Antagonists, including Zileuton and others;

Methylxanthines, including:

Caffeine, preferably at a dosage range of from about 65 to about 600 mg; Theophylline, preferably at a dosage range of from about 25 to about 1,200 mg; Enprofylline; Pentoxifylline, preferably at a dosage range of from about 400 to about 3,600 mg; Aminophylline, preferably at a dosage range of from about 50 to about 800 mg; Dyphylline, preferably at a dosage range of from about 200 to about 1,600 mg and others;

Antioxidants or radical inhibitors, including: Ascorbic acid, preferably at a dosage range of from about 50 to about 10,000 mg; Tocopherol, preferably at a dosage range of from about 50 to about 2,000 mg; Ethanol, preferably at a dosage range of from about 500 to about 10,000 mg and others;

Steroids, Preferably intranasally administered steroids, including: Beclomethasone, preferably at a dosage range of from about 84 to about 336 µg; Fluticasone, preferably at a dosage range of from about 50 to about 400 µg; Budesonide, preferably at a dosage range of from about 64 to about 256 µg; Mometasone, preferably at a dosage range of from about 50 to about 300 mg; Triamcinolone, preferably at a dosage range of from about 110 to about 440 µg; Dexamethasone, preferably at a dosage range of from about 168 to about 1,008 µg; Flunisolide, preferably at a dosage range of from about 50 to about 300 µg; Prednisone (preferably oral), preferably at a dosage range of from about 5 to about 60 mg; Hydrocortisone (preferably oral), preferably at a dosage range of from about 20 to about 300 mg and others;

Bronchodilators, Preferably for inhalation, including:
Albuterol, preferably at a dosage range of from about 90 to about 1,080 µg; 2 to about 16 mg (if dosed orally); Epinephrine, preferably at a dosage range of from about 220 to about 1,320 µg; Ephedrine, preferably at a dosage range of from about 15 to about 240 mg (if dosed orally); 250 to about 1,000 µg (if dosed intranasally); Metaproterenol, preferably at a dosage range of from about 65 to about 780 µg or 10 to about 80 mg if dosed orally; Terbutaline, preferably at a dosage range of from about 200 to about 2,400 µg; 2.5 to about 20 mg (if dosed orally); Isoetharine, preferably at a dosage range of from about 340 to about 1,360 µg; Pirbuterol, preferably at a dosage range of from about 200 to about 2,400 µg; Bitolterol, preferably at a dosage range of from about 370 to about 2,220 µg; Fenoterol, preferably at a dosage range of from about 100 to about 1,200 µg; 2.5 to about 20 mg (if dosed orally); Rimeterol, preferably at a dosage range of from about 200 to about 1,600 µg; Ipratroprium, preferably at a dosage range of from about 18 to about 216 µg (inhalation) and others; and Antivirals, including:
Amantadine, preferably at a dosage range of from about 50 to about 200 mg; Rimantadine, preferably at a dosage range of from about 50 to about 200 mg; Enviroxime; Nonoxinols, preferably at a dosage range of from about 2 to about 20 mg (preferably an intranasal form); Acyclovir, preferably at a dosage range of from about 200 to about 2,000 mg (oral); 1 to about 10 mg (preferably an intranasal form); Alpha-Interferon, preferably at a dosage range of from about 3 to about 36 MIU; Beta-Interferon, preferably at a dosage range of from about 3 to about 36 MIU and others;

Ocular Drug actives: acetylcholinesterase inhibitors, e.g., echothiophate from about 0.03% to about 0.25% in topical solution and others; and Gastrointestinal actives: antidiarrheals, e.g., loperamide from about 0.1 mg to about 1.0 mg per dose, and bismuth subsalicylate from about 25 mg to about 300 mg per dose and others.

Of course, clearly contemplated and included in the description above are the acid or base addition salts, esters, metabolites, stereoisomers and enantiomers of these preferred combination actives, as well as their analogues of these actives that are safe and effective. It is also recognized that an active may be useful for more than one of the above uses, and these uses are clearly contemplated as well. This overlap is recognized in the art and adjusting dosages and the like to fit the indication is well within the purview of the skilled medical practitioner.

Methods of Use

Without being bound by theory, it is contemplated that the primary mechanism by which alpha-2 agonists provide efficacy is by intervening in the biological cascade responsible for disorder(s) and/or manifestation(s) thereof. It may be that there is no deficit in alpha-2 adrenoceptor activity: such activity may be normal. However, administration of an alpha-2 agonist may be a useful way of rectifying a disorder, condition or manifestation thereof.

Thus as used herein, the terms "disease," "disorder" and "condition" are used interchangeably to refer to maladies related to or modulated by alpha-2 adrenoceptor activity.

As used herein, a disorder described by the terms "modulated by alpha-2 adrenoceptors," or "modulated by alpha-2 adrenoceptor activity" refers to a disorder, condition or disease where alpha-2 adrenoceptor activity is an effective means of alleviating the disorder or one or more of the biological manifestations of the disease or disorder; or interferes with one or more points in the biological cascade either leading to the disorder or responsible for the underlying disorder; or alleviates one or more symptoms of the disorder. Thus, disorders subject to "modulation" include those for which:

The lack of alpha-2 activity is a "cause" of the disorder or one or more of the biological manifestations, whether the activity was altered genetically, by infection, by irritation, by internal stimulus or by some other cause;

The disease or disorder or the observable manifestation or manifestations of the disease or disorder are alleviated by alpha-2 activity. The lack of alpha-2 activity need not be causally related to the disease or disorder or the observable manifestations thereof;

Alpha-2 activity interferes with part of the biochemical or cellular cascade that results in or relates to the disease or disorder. In this respect, the alpha-2 activity alters the cascade, and thus controls the disease, condition or disorder.

The compounds of this invention are particularly useful for the treatment of nasal congestion associated with allergies, colds, and other nasal disorders, as well as the sequelae of congestion of the mucous membranes (for example, sinusitis and otitis media). At effective doses, it has been found that undesired side effects can be avoided.

While not limited to a particular mechanism of action, the subject compounds are believed to provide advantages in the treatment of nasal decongestion over related compounds through their ability to interact with alpha-2 adrenoceptors. The subject compounds have been found to be alpha-2 adrenoceptor agonists which cause constriction of peripheral vascular beds in the nasal turbinates.

Alpha-2 adrenoceptors are distributed both inside and outside of the central nervous system. Thus, though not essential for activity or efficacy, certain disorders preferably are treated with compounds that act on alpha-2 adrenoceptors in only one of these regions. Compounds of this invention vary in their ability to penetrate into the central nervous system and, thus, to produce effects mediated through central alpha-2 adrenoceptors. Thus, for example, a compound which displays a higher degree of central nervous system activity is preferred for central nervous system indications over other compounds as described below. However, even for compounds that exhibit primarily peripheral activity, central nervous system actions can be evoked by an increase in the dose of the compound. Further specificity of action of these compounds can be achieved by delivering the agent to the region where activity is desired (for example, topical administration to the eye, nasal mucosa or respiratory tract).

Compounds preferred for, but not limited to, the treatment of certain cardiovascular disorders, pain, substance abuse and/or withdrawal, ulcer and hyperacidity include those compounds that are centrally acting. By centrally acting what is meant is that they have some action on the alpha-2 adrenoceptors in the central nervous system in addition to their action at peripheral alpha-2 adrenoceptors.

Compounds preferred for, but not limited to, the treatment of respiratory disorders, ocular disorders, migraine, certain cardiovascular disorders, and certain other gastrointestinal disorders are peripherally acting. By peripherally acting, what is meant is that these compounds act primarily on alpha-2 adrenoceptors in the periphery, rather than those in the central nervous system. Methods are available in the art to determine which compounds are primarily peripherally acting and which are primarily centrally acting.

Thus, compounds of the subject invention are also useful for the treatment of ocular disorders such as ocular hypertension, glaucoma, hyperemia, conjunctivitis, and uveitis. The compounds are administered either perorally, or topically as drops, sprays, mists, gels or creams directly to the surface of the mammalian eye.

The compounds of this invention are also useful for controlling gastrointestinal disorders, such as diarrhea, irritable bowel syndrome, hyperchlorhydria and peptic ulcer.

The compounds of this invention are also useful for diseases and disorders associated with sympathetic nervous system activity, including hypertension, myocardial ischemia, cardiac reperfusion injury, angina, cardiac arrhythmia, heart failure and benign prostatic hypertrophy. Due to their sympatholytic effect, compounds are also useful as an adjunct to anesthesia during surgical procedures.

The compounds of this invention are also useful for relieving pain associated with various disorders. The compounds are administered perorally, parenterally, and/or by direct injection into the cerebrospinal fluid.

The compounds of this invention are also useful for the prophylactic or acute treatment of migraine. The compounds are administered perorally, parenterally or intranasally.

The compounds of this invention are also useful for treatment of substance abuse, in particular abuse of alcohol and opiates, and alleviating the abstinence syndromes evoked by withdrawal of these substances.

The compounds of this invention are also useful for other diseases and disorders where vasoconstriction, particularly of veins, would provide a benefit, including septic or cardiogenic shock, elevated intracranial pressure, hemmorhoids, venous insufficiency, varicose veins, and menopausal flushing.

The compounds of this invention are also useful for neurologic diseases and disorders, including spasticity, epilepsy, attention deficit hyperactive disorder, Tourette's syndrome, and cognitive disorders.

The pharmacological activity and selectivity of these compounds can be determined using published test procedures. The alpha-2 selectivity of the compounds is determined by measuring receptor binding affinities and in vitro functional potencies in a variety of tissues known to possess alpha-2 and/or alpha-1 receptors. (See, e.g., The *Alpha-2 Adrenergic Receptors*, L. E. Limbird, ed., Humana Press, Clifton, N.J.) The following in vivo assays are typically conducted in rodents or other species. Central nervous system activity is determined by measuring locomotor activity as an index of sedation. (See, e.g., Spyraki, C. & H. Fibiger, "Clonidine-induced Sedation in Rats: Evidence for Mediation by Postsynaptic Alpha-2 Adrenoreceptors", *Journal of Neural Transmission*, Vol. 54 (1982), pp. 153–163). Nasal decongestant activity is measured using rhinomanometry as an estimate of nasal airway resistance. (See, e.g., Salem, S. & E. Clemente, "A New Experimental Method for Evaluating Drugs in the Nasal Cavity", *Archives of Otolaryngology*, Vol. 96 (1972), pp. 524–529). Antiglaucoma activity is determined by measuring intraocular pressure. (See, e.g., Potter, D., "Adrenergic Pharmacology of Aqueous Human Dynamics", *Pharmacological Reviews*, Vol. 13 (1981), pp. 133–153). Antidiarrheal activity is determined by measuring the ability of the compounds to inhibit prostaglandin-induced diarrhea. (See, e.g., Thollander, M., P. Hellstrom & T. Svensson, "Suppression of Castor Oil-Induced Diarrhea by Alpha-2 Adrenoceptor Agonists", *Alimentary Pharmacology and Therapeutics*, Vol. 5 (1991), pp. 255–262). Efficacy in treating irritable bowel syndrome is determined by measuring the ability of compounds to reduce the stress-induced increase in fecal output. (See, e.g., Barone, F., J. Deegan, W. Price, P. Fowler, J. Fondacaro & H. Ormsbee ll, "Cold-restraint stress increases rat fecal pellet output and colonic transit", *American Journal of Physiology*, Vol. 258 (1990), pp. G329–G337). Antiulcer and reduction of hyperchlorhydria efficacy is determined by measuring the reduction in gastric acid secretion produced by these compounds (See, e.g., Tazi-Saad, K., J. Chariot, M. Del Tacca & C. Roze, "Effect of $\alpha$2-adrenoceptor agonists on gastric pepsin and acid secretion in the rat", *British Journal of Pharmacology*, Vol. 106 (1992), pp. 790–796). Antiasthma activity is determined by measuring the effect of the compound on bronchoconstriction associated with pulmonary challenges such as inhaled antigens. (See, e.g., Chang, J. J. Musser & J. Hand, "Effects of a Novel Leukotriene $D_4$ Antagonist with 5-Lipoxygenase and Cyclooxygenase Inhibitory Activity, Wy45,911, on Leukotriene-$D_4$- and Antigen-Induced Bronchoconstriction in Guinea Pig", *International Archives of Allergy and Applied Immunology*, Vol. 86 (1988), pp. 48–54; and Delehunt, J., A. Perruchound, L. Yerger, B. Marchette, J. Stevenson & W. Abraham, "The Role of Slow-Reacting Substance of Anaphylaxis in the Late Bronchial Response After Antigen Challenge in Allergic Sheep", *American Reviews of Respiratory Disease*, Vol. 130 (1984), pp. 748–754). Activity in cough is determined by measuring the number and latency of the cough response to respiratory challenges such as inhaled citric acid. (See, e.g., Callaway, J. & R. King, "Effects of Inhaled $\alpha$2-Adrenoceptor and $GABA_B$ Receptor Agonists on Citric Acid-Induced Cough and Tidal Volume Changes in Guinea Pigs", *European Journal of Pharmacology*, Vol. 220 (1992), pp. 187–195). The sympatholytic activity of these compounds is determined by measuring the reduction of plasma catecholamines (See, e.g., R. Urban, B. Szabo & K. Starke "Involvement of peripheral presynaptic inhibition in the reduction of sympathetic tone by moxonidine, rilmenidine and UK 14,304", *European Journal of Pharmacology*, Vol. 282 (1995), pp. 29–37) or the reduction in renal sympathetic nerve activity (See, e.g., Feng, Q., S. Carlsson, P. Thoren & T. Hedner, "Effects of clonidine on renal sympathetic nerve activity, natriuresis and diuresis in chronic congestive heart failure rats", *Journal of Pharmacology and Experimental Therapeutics*, Vol. 261 (1992), pp. 1129–1135), providing the basis for their benefit in heart failure and benign prostatic hypertrophy. The hypotensive effect of these compounds is measure directly as a reduction in mean blood pressure (See, e.g., Timmermans, P. & P. Van Zwieten, "Central and peripheral α-adrenergic effects of some imidazolidines", *European Journal of Pharmacology*, Vol. 45 (1977), pp. 229–236). Clinical studies have demonstrated the beneficial effect of alpha-2 agonists in the prevention of myocardial ischemia during surgery (See, e.g., Talke, P., J. Li, U. Jain, J. Leung, K. Drasner, M. Hollenberg & D. Mangano, "Effects of Perioperative Dexmedetomidine Infusion in Patients Undergoing Vascular Surgery", *Anesthesiology*, Vol. 82 (1995), pp. 620–633) and in the prevention of angina (See, e.g., Wright, R.A., P. Decroly, T. Kharkevitch & M. Oliver, "Exercise Tolerance in Angina is Improved by Mivazerol—an α2-Adrenoceptor Agonist", *Cardiovascular Drugs and Therapy*, Vol. 7 (1993), pp. 929–934). The efficacy of these compounds in cardiac reperfusion injury is demonstrated by measuring the reduction of cardiac necrosis and neutrophil infiltration (See, e.g., Weyrich, A., X. Ma, & A. Lefer, "The Role of L-Arginine in Ameliorating Reperfusion Injury After Myocardial Ischemia in the Cat", *Circulation*, Vol. 86 (1992), pp. 279–288). The cardiac antiarrhythmic effect of these compounds is demonstrated by measuring the inhibition of ouabain induced arrhythmias (See, e.g., Thomas, G. & P. Stephen, "Effects of Two Imidazolines (ST-91 and ST-93) on the Cardiac Arrhythmias and Lethality Induced by Ouabain in Guinea-Pig", *Asia-Pacific Journal of Pharmacology*, Vol. 8 (1993), pp.109–113; and Samson, R., J. Cai, E. Shibata, J. Martins & H. Lee, "Electrophysiological effects of α2-adrenergic stimulation in canine cardiac Purkinje fibers", *American Journal of Physiology*, Vol. 268 (1995), pp. H2024–H2035). The vasoconstrictor activity of these compounds is demonstrated by measuring the contractile properties on isolated arteries and veins in vitro (See, e.g., Flavahan, N., T. Rimele, J. Cooke & M. Vanhoutte, "Characterization of Postjunctional Alpha-1 and Alpha-2 Adrenoceptors Activated by Exogenous or Nerve-Released Norepinephrine in the Canine Saphenous Vein", *Journal of Pharmacology and Experimental Therapeutics*, Vol. 230 (1984), pp. 699–705). The effectiveness of these compounds at reducing intracranial pressure is demonstrated by measurement of this property in a canine model of subarachnoid hemorrhage (See, e.g., McCormick, J., P. McCormick, J. Zabramski & R. Spetzler, "Intracranial pressure reduction by a central alpha-2 adrenoreceptor agonist after subarachnoid hemorrhage", *Neurosurgery*, Vol. 32 (1993), pp. 974–979). The inhibition of menopausal flushing is demonstrated by measuring the reduction of facial blood flow in the rat (See, e.g., Escott, K., D. Beattie, H. Connor & S. Brain, "The modulation of the increase in rat facial skin blood flow observed after trigeminal ganglion stimulation", *European Journal of Pharmacology*, Vol. 284 (1995), pp. 69–76) as demonstrated for alpha-2 adrenergic agonists on cutaneous blood flow in the tail (See, e.g., Redfern, W., M. MacLean, R. Clague & J. McGrath, "The role of alpha-2 adrenoceptors in the vasculature of the rat tail", *British Journal of Pharmacology*, Vol. 114 (1995), pp. 1724–1730). The antinociceptive and pain reducing properties of these compounds is demonstrated by measuring the increase in pain threshold in the rodent writhing and hot plate antinociceptive models (See, e.g., Millan, M., K. Bervoets, J. Rivet, R. Widdowson, A. Renouard, S, Le Marouille-Girardon & A. Gobert, "Multiple Alpha-2 Adrenergic Receptor Subtypes. II. Evidence for a Role of Rat Alpha-2A Adrenergic Receptors in the Control of Nociception, Motor Behavior and Hippocampal Synthesis of Noradrenaline", *Journal of Pharmacology and Experimental Therapeutics*, Vol. 270 (1994), pp. 958–972). The antimigraine effect of these compounds is demonstrated by measuring the reduction of dural neurogenic inflammation to trigeminal ganglion stimulation in the rat (See, e.g., Matsubara, T., M. Moskowitz & Z. Huang, "UK-14,304, R(-)-alpha-methyl-histamine and SMS 201-995 block plasma protein leakage within dura mater by prejunctional mechanisms", *European Journal of Pharmacology*, Vol. 224 (1992), pp. 145–150). The ability of these compounds to suppress opiate withdrawal is demonstrated by measuring the suppression of enhanced sympathetic nerve activity (See, e.g., Franz, D., D. Hare & K. McCloskey, "Spinal sympathetic neurons: possible sites of opiate-withdrawal suppression by clonidine", *Science*, Vol. 215 (1982), pp. 1643–1645). Antiepileptic activity of these compounds is demonstrated by measuring the inhibition of the kindling response (See, e.g., Shouse, M., M. Bier, J. Langer, O. Alcalde, M. Richkind & R. Szymusiak, "The α2-agonist clonidine suppresses seizures, whereas the alpha-2 antagonist idazoxan promotes seizures—a microinfusion study in amygdala-kindled kittens", *Brain Research*, Vol. 648 (1994), pp. 352–356). The effectiveness of other alpha-2 agonists in the management of neurologic disorders has been demonstrated, including attention-deficit hyperactive disorder and Tourette's syndrome (See, e.g., Chappell P., M. Riddle, L. Scahill, K. Lynch, R. Schultz, A. Arnsten, J. Leckman & D. Cohen, "Guanfacine treatment of comorbid attention-deficit hyperactivity disorder and Tourette's syndrome: preliminary clinical experience", *Journal of American Academy of Child and Adolescent Psychiatry*, Vol. 34 (1995), pp. 1140–1146), cognitive disorders (See, e.g., Coull, J., "Pharmacological manipulations of the α2-noradrenergic system. Effects on cognition", *Drugs and Aging*, Vol.5 (1994), pp.116–126), and spasticity (See, e.g., Eyssette, M., F. Rohmer, G. Serratrice, J. Warter & D. Boisson, "Multicenter, double-blind trial of a novel antispastic agent, tizanidine, in spasticity associated with multiple sclerosis", *Current Medical Research & Opinion*, Vol. 10 (1988), pp. 699–708).

Another aspect of this invention involves methods for preventing or treating nasal congestion by administering a safe and effective amount of a subject compound to a mammal experiencing or at risk of experiencing nasal congestion. Such nasal congestion may be associated with human diseases or disorders which include, but are not limited to, seasonal allergic rhinitis, acute upper respiratory viral infections, sinusitis, perennial rhinitis, and vasomotor rhinitis. In addition, other disorders can be generally associated with mucous membrane congestion (for example, otitis media and sinusitis.) Each administration of a dose of the subject compound preferably administers a dose within the range of from about 0.0001 mg/kg to about 5 mg/kg of a compound, more preferably from about 0.001 mg/kg to about 0.5 mg/kg. Peroral administration of such doses is preferred. The frequency of administration of a subject compound according to this invention is preferably from about once to about six times daily, more preferably from about once to about 4 times daily. Such doses and frequencies are also preferred for treating other respiratory conditions, such as, cough, chronic obstructive pulmonary disease (COPD) and asthma. Such doses and frequencies are also preferred for treating conditions that are associated with mucous membrane congestion (for example, sinusitis and otitis media).

Another aspect of this invention involves methods for preventing or treating glaucoma by administering a safe and effective amount of a subject compound to a mammal experiencing or at risk of experiencing glaucoma. If administered systemically, each administration of a dose of the subject compound preferably administers a dose within the range of from about 0.0001 mg/kg to about 5 mg/kg of a compound, more preferably from about 0.001 mg/kg to about 0.5 mg/kg. If intraocular dosing is used then preferably one administers a typical volume (for example, 1 or 2 drops) of a liquid composition, comprising from about 0.0001% to about 5% of a subject compound, more preferably from about 0.01% to about 0.5% of the compound. Determination of the exact dosage and regimen is within the purview of the skilled artisan. Intraocular administration of such doses is preferred. The frequency of administration of a subject compound according to this invention is preferably from about once to about six times daily, more preferably from about once to about 4 times daily.

Another aspect of this invention involves methods for preventing or treating gastrointestinal disorders, such as diarrhea, irritable bowel syndrome, and peptic ulcer by administering a safe and effective amount of a subject compound to a mammal experiencing or at risk of experiencing gastrointestinal disorders. Each administration of a dose of the subject compound preferably administers a dose within the range of from about 0.0001 mg/kg to about 5 mg/kg of a compound, more preferably from about 0.001 mg/kg to about 0.5 mg/kg. Peroral administration of such doses is preferred. The frequency of administration of a subject compound according to this invention is preferably from about once to about six times daily, more preferably from about once to about 4 times daily.

Another aspect of this invention involves methods for preventing or treating migraine, by administering a safe and effective amount of a subject compound to a mammal experiencing or at risk of experiencing migraine. Each administration of a dose of the subject compound preferably administers a dose within the range of from about 0.0001 mg/kg to about 5 mg/kg of a compound, more preferably from about 0.001 mg/kg to about 0.5 mg/kg. Peroral, parenteral or intranasal administration of such doses is preferred. The frequency of peroral administration of a subject compound according to this invention is preferably from about once to about six times daily, more preferably from about once to about 4 times daily. The frequency of parenteral dosing of a subject compound according to this invention is preferably from about once to about six times daily, more preferably from about once to about 4 times daily or by infusion to the desired effect. The frequency of intranasal dosing of a subject compound according to this invention is preferably from about once to about six times daily, more preferably from about once to about 4 times daily.

Another aspect of this invention involves methods for preventing or treating disorders related to sympathetic nervous system activity, such as hypertension, myocardial ischemia, cardiac reperfusion injury, angina, cardiac arrhythmia, and benign prostatic hypertrophy, by administering a safe and effective amount of a subject compound to a mammal experiencing or at risk of experiencing these diseases or disorders. Each administration of a dose of the subject compound preferably administers a dose within the range of from about 0.0001 mg/kg to about 5 mg/kg of a compound, more preferably from about 0.001 mg/kg to about 0.5 mg/kg. Peroral and parenteral administration of such doses are preferred. The frequency of peroral administration of a subject compound according to this invention is preferably from about once to about six times daily, more preferably from about once to about 4 times daily. The frequency of parenteral dosing of a subject compound according to this invention is preferably from about once to about six times daily, more preferably from about once to about 4 times daily or by infusion to the desired effect.

Another aspect of this invention involves methods for preventing or treating pain, by administering a safe and effective amount of a subject compound to a mammal experiencing or at risk of experiencing pain. Each administration of a dose of the subject compound preferably administers a dose within the range of from about 0.0001 mg/kg to about 5 mg/kg of a compound, more preferably from about 0.001 mg/kg to about 0.5 mg/kg. Peroral or parenteral administration of such doses is preferred. The frequency of peroral administration of a subject compound according to this invention is preferably from about once to about six times daily, more preferably from about once to about 4 times daily. The frequency of parenteral dosing of a subject compound according to this invention is preferably from about once to about six times daily, more preferably from about once to about 4 times daily or by infusion to the desired effect.

Another aspect of this invention involves methods for preventing or treating substance abuse and the abstinence syndrome resulting from withdrawal of these substances, such as alcohol and opiates, by administering a safe and effective amount of a subject compound to a mammal experiencing or at risk of experiencing substance abuse or withdrawal symptoms. Each administration of a dose of the subject compound preferably administers a dose within the range of from about 0.0001 mg/kg to about 5 mg/kg of a compound, more preferably from about 0.001 mg/kg to about 0.5 mg/kg. Peroral administration of such doses is preferred. The frequency of administration of a subject compound according to this invention is preferably from about once to about six times daily, more preferably from about once to about 4 times daily.

Composition and Method Examples

The following non-limiting examples illustrate the compositions and methods of use of this invention.

Example A

Oral Tablet Composition

| Ingredient | Amount per tablet (mg) |
| --- | --- |
| Subject Compound 4 | 20.0 |
| Microcrystalline cellulose (Avicel PH 102 ®) | 80.0 |
| Dicalcium phosphate | 96.0 |
| Pyrogenic silica (Cab-O-Sil ®) | 1.0 |
| Magnesium stearate | 3.0 |
| Total = | 200.0 mg |

One tablet is swallowed by a patient with nasal congestion. The congestion is substantially diminished.

Other compounds having a structure according to Formula 1 are used with substantially similar results.

Example B

Chewable Tablet Composition

| Ingredient | Amount per tablet (mg) |
| --- | --- |
| Subject Compound 1 | 15.0 |
| Mannitol | 255.6 |
| Microcrystalline cellulose (Avicel PH 101 ®) | 100.8 |
| Dextrinized sucrose (Di-Pac ®) | 199.5 |
| Imitation orange flavor | 4.2 |
| Sodium saccharin | 1.2 |
| Stearic acid | 15.0 |
| Magnesium stearate | 3.0 |
| FD&C Yellow #6 dye | 3.0 |
| Pyrogenic silica (Cab-O-Sil ®) | 2.7 |
| Total = | 600.0 mg |

One tablet is chewed and swallowed by a patient with nasal congestion. The congestion is substantially reduced.

Other compounds having a structure according to Formula 1 are used with substantially similar results.

Example C

Sublingual Tablet Composition

| Ingredient | Amount per tablet (mg) |
| --- | --- |
| Subject Compound 5 | 2.00 |
| Mannitol | 2.00 |
| Microcrystalline cellulose (Avicel PH 101 ®) | 29.00 |
| Mint flavorants | 0.25 |
| Sodium saccharin | 0.08 |
| Total = | 33.33 mg |

One tablet is placed under the tongue of a patient with nasal congestion and allowed to dissolve. The congestion is rapidly and substantially diminished.

Other compounds having a structure according to Formula 1 are used with substantially similar results.

Example D

Intranasal Solution Composition

| Ingredient | Composition (% w/v) |
| --- | --- |
| Subject Compound 3 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

One-tenth of a mL of the composition is sprayed from a pump actuator into each nostril of a patient with nasal congestion. The congestion is substantially diminished.

Other compounds having a structure according to Formula 1 are used with substantially similar results.

Example E

Intranasal Gel Composition

| Ingredient | Composition (% w/v) |
| --- | --- |
| Subject Compound 1 | 0.10 |
| Benzalkonium chloride | 0.02 |
| Thimerosal | 0.002 |
| Hydroxypropyl methylcellulose (Metolose 65SH40000 ®) | 1.00 |
| Aromatics | 0.06 |
| Sodium chloride (0.65%) | q.s. |
| Total = | 100.00 |

One-fifth of a mL of the composition is applied as drops from a dropper into each nostril of a patient with nasal congestion. The congestion is substantially reduced.

Other compounds having a structure according to Formula 1 are used with substantially similar results.

Example F

Inhalation Aerosol Composition

| Ingredient | Composition (% w/v) |
| --- | --- |
| Subject Compound 2 | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

Two-puffs of the aerosol composition is inhaled from a metered-dose inhaler by a patient with asthma. The asthmatic condition is effectively relieved.

Other compounds having a structure according to Formula 1 are used with substantially similar results.

Example G

Topical Ophthalmic Composition

| Ingredient | Composition (% w/v) |
| --- | --- |
| Subject Compound 5 | 0.10 |
| Benzalkonium chloride | 0.01 |
| EDTA | 0.05 |
| Hydroxyethylcellulose (Natrosol M ®) | 0.50 |
| Sodium metabisulfite | 0.10 |
| Sodium chloride (0.9%) | q.s. |
| Total = | 100.0 |

One-tenth of a mL of the composition is administered directly into each eye of a patient with glaucoma. The intraocular pressure is substantially reduced.

Other compounds having a structure according to Formula 1 are used with substantially similar results.

Example H

Oral Liquid Composition

| Ingredient | Amount/15 mL Dose |
| --- | --- |
| Subject Compound 4 | 15 mg |
| Chlorpheniramine maleate | 4 mg |
| Propylene glycol | 1.8 g |
| Ethanol (95%) | 1.5 mL |
| Methanol | 12.5 mg |
| Eucalyptus oil | 7.55 mg |
| Flavorants | 0.05 mL |
| Sucrose | 7.65 g |
| Carboxymethylcellulose (CMC) | 7.5 mg |
| Microcrystalline cellulose and Sodium CMC (Avicel RC 591 ®) | 187.5 mg |
| Polysorbate 80 | 3.0 mg |
| Glycerin | 300 mg |
| Sorbitol | 300 mg |
| FD&C Red #40 dye | 3 mg |
| Sodium saccharin | 22.5 mg |
| Sodium phosphate monobasic | 44 mg |
| Sodium citrate monohydrate | 28 mg |
| Purified Water | q.s. |
| Total = | 15 mL |

One 15 mL dose of the liquid composition is swallowed by a patient with nasal congestion and runny nose due to allergic rhinitis. The congestion and runny nose are effectively reduced.

Other compounds having a structure according to Formula 1 are used with substantially similar results.

Example J

Oral Liquid Composition

| Ingredient | Amount/15 mL Dose |
| --- | --- |
| Subject Compound 2 | 30 mg |
| Sucrose | 8.16 g |
| Glycerin | 300 mg |
| Sorbitol | 300 mg |
| Methylparaben | 19.5 mg |
| Propylparaben | 4.5 mg |
| Menthol | 22.5 mg |
| Eucalyptus oil | 7.5 mg |
| Flavorants | 0.07 mL |
| FD&C Red #40 dye | 3.0 mg |
| Sodium saccharin | 30 mg |
| Purified water | q.s. |
| Total = | 15 mL |

One 15 mL dose of the alcohol-free liquid medication is swallowed by a patient with nasal congestion. The congestion is substantially diminished.

Other compounds having a structure according to Formula 1 are used with substantially similar results.

Example K

Oral Tablet Composition

| Ingredient | Amount per tablet (mg) |
| --- | --- |
| Subject Compound 1 | 4 |
| Microcrystalline cellulose, NF | 130 |
| Starch 1500, NF | 100 |
| Magnesium stearate, USP | 2 |
| Total = | 236 mg |

One tablet is swallowed by a patient with migraine. The pain and aura of migraine is substantially diminished.

Other compounds having a structure according to Formula 1 are used with substantially similar results.

Example L

Oral Tablet Composition

| Ingredient | Amount per tablet (mg) |
| --- | --- |
| Subject Compound 2 | 12 |
| Hydroxypropyl methylcellulose, USP | 12 |
| Magnesium stearate, USP | 2 |
| Lactose anhydrous, USP | 200 |
| Total = | 226 mg |

For the relief of pain. Adults 12 and over take one tablet every twelve hours.

Other compounds having a structure according to Formula 1 are used with substantially similar results.

Example M

Oral Caplet Composition

| Ingredient | Amount per tablet (mg) |
| --- | --- |
| Naproxen sodium anhydrous, USP | 220 |
| Subject Compound 3 | 6 |
| Hydroxypropyl methylcellulose, USP | 6 |
| Magnesium stearate, USP | 2 |
| Povidone K-30, USP | 10 |
| Talc, USP | 12 |
| Microcrystalline cellulose, NF | 44 |
| Total = | 300 mg |

For relief of symptoms associated with the common cold, sinusitis, or flu including nasal congestion, headache, fever, body aches, and pains. Adults 12 and over take two caplets every twelve hours.

Other compounds having a structure according to Formula 1 are used with substantially similar results.

Example N

Oral Tablet Composition

| Ingredient | Amount per tablet (mg) |
| --- | --- |
| Subject Compound 4 | 6 |
| Hydroxypropyl methylcellulose, USP | 6 |
| Silicon dioxide, colloidal, NF | 30 |
| Pregelatinized starch, NF | 50 |
| Magnesium stearate, USP | 4 |
| Total = | 96 mg |

For treatment of benign prostatic hypertrophy. Take one tablet per day.

Other compounds having a structure according to Formula 1 are used with substantially similar results.

Example O

Oral Tablet Composition

| Ingredient | Amount per caplet (mg) |
|---|---|
| Subject Compound 5 | 6 |
| Hydroxypropyl methylcellulose, USP | 6 |
| Magnesium stearate, USP | 2 |
| Povidone K-30, USP | 10 |
| Talc, USP | 12 |
| Microcrystalline cellulose, NF | 44 |
| Total = | 80 mg |

For the use in the treatment of alcoholism or opiate addiction. Adults 12 and over take two caplets every twelve hours.

Other compounds having a structure according to Formula 1 are used with substantially similar results.

Example P

Oral Tablet Composition

| Ingredient | Amount per tablet (mg) |
|---|---|
| Subject Compound 1 | 6 |
| Hydroxypropyl methylcellulose, USP | 12 |
| Magnesium stearate, USP | 2 |
| Povidone K-30, USP | 10 |
| Talc, USP | 12 |
| Microcrystalline cellulose, NF | 44 |
| Total = | 86 mg |

For the treatment of ulcer and hyperacidity. Take two tablets as appropriate.

Other compounds having a structure according to Formula 1 are used with substantially similar results.

Example Q

Oral Tablet Composition

| Ingredient Component | Amount per tablet (mg) Amount |
|---|---|
| Subject Compound 5 | 10 mg/ml carrier |
| Carrier: | |
| Sodium citrate buffer with | |
| (percent by weight of carrier): | |
| Lecithin | 0.48% |
| Carboxymethylcellulose | 0.53 |
| Povidone | 0.50 |
| Methyl paraben | 0.11 |
| Propyl paraben | 0.011 |

For the reduction of cardiac reperfusion injury.

Other compounds having a structure according to Formula 1 are used with substantially similar results.

Example R

Oral Liquid Composition

| Ingredient | Amount/fl oz Dose (mg) |
|---|---|
| Acetaminophen, USP | 1000 |
| Doxylamine succinate, USP | 12.5 |
| Dextromethorphan hydrobromide, USP | 30 |
| Subject Compound 2 | 6 |
| Dow XYS-40010.00 resin | 3 |
| High fructose corn syrup | 16000 |
| Polyethylene glycol, NF | 3000 |
| Propylene glycol, USP | 3000 |
| Alcohol, USP | 2500 |
| Sodium citrate dihydrate, USP | 150 |
| Citric acid, anhydrous, USP | 50 |
| Saccharin sodium, USP | 20 |
| Flavor | 3.5 |
| Purified water, USP | 3500 |
| Total = | 29275 mg/fl oz |

For the relief of minor aches, pains, headache, muscular aches, sore throat pain, and fever associated with a cold or flu. Relieves nasal congestion, cough due to minor throat and bronchial irritations, runny nose, and sneezing associated with the common cold. Adults 12 and over take one fluid ounce every six hours.

Other compounds having a structure according to Formula 1 are used with substantially similar results.

Example S

Oral Liquid Composition

| Ingredient | Amount/fl oz Dose (mg) |
|---|---|
| Naproxen sodium anhydrous, USP | 220 |
| Doxylamine succinate, USP | 12.5 |
| Dextromethorphan hydrobromide, USP | 30 |
| Subject Compound 1 | 6 |
| Dow XYS-40010.00 resin | 3 |
| High fructose corn syrup | 16000 |
| Polyethylene glycol, NF | 3000 |
| Propylene glycol, USP | 3000 |
| Alcohol, USP | 2500 |
| Sodium citrate dihydrate, USP | 150 |
| Citric acid, anhydrous, USP | 50 |
| Saccharin sodium, USP | 20 |
| Flavor | 3.5 |
| Purified water, USP | 3800 |
| Total = | 28795 mg/fl oz |

For the relief of minor aches, pains, headache, muscular aches, sore throat pain, and fever associated with a cold or flu. Relieves nasal congestion, cough due to minor throat and bronchial irritations, runny nose, and sneezing associated with the common cold. Adults 12 and over take one fluid ounce every six hours.

Other compounds having a structure according to Formula 1 are used with substantially similar results.

COMPOSITION EXAMPLE T

A composition for parenteral administration, according to this invention, is made comprising:

| Component | Amount |
| --- | --- |
| Subject Compound I | 10 mg/ml carrier |
| Carrier: | |
| Sodium citrate buffer with | |
| (percent by weight of carrier): | |
| Lecithin | 0.48% |
| Carboxymethylcellulose | 0.53 |
| Povidone | 0.50 |
| Methyl paraben | 0.11 |
| Propyl paraben | 0.011 |

The above ingredients are mixed, forming a solution. Approximately 2.0 ml of the solution is administered, intravenously, to a human subject suffering from septic or cardiogenic shock. The symptoms subside.

Other compounds having a structure according to Formula 1 are used with substantially similar results.

Example U

Oral Tablet Composition

| Ingredient | Amount per tablet (mg) |
| --- | --- |
| Subject compound 5 | 10 |
| Hydroxypropyl methylcellulose, USP | 12 |
| Magnesium stearate, USP | 2 |
| Povidone K-30, USP | 10 |
| Talc, USP | 12 |
| Microcrystalline cellulose, NF | 44 |
| Total = | 90 mg |

For the treatment of cardiac arrhythmia. Take as prescribed.

Other compounds having a structure according to Formula 1 are used with substantially similar results.

Example V

Oral Tablet Composition

| Ingredient | Amount per tablet (mg) |
| --- | --- |
| Subject Compound 1 | 4 |
| Microcrystalline cellulose, NF | 130 |
| Starch 1500, NF | 100 |
| Magnesium stearate, USP | 2 |
| Total = | 236 mg |

For the treatment of congestive heart failure. Take as prescribed.

Other compounds having a structure according to Formula 1 are used with substantially similar results.

Modification of the preceding embodiments is within the scope of the skilled artisan in formulation, given the guidance of the specification in light of the state of the art.

Other examples of combination actives are contemplated. Examples of medicaments which can be combined with the primary active are included in U.S. Pat. No. 4,552,899 to Sunshine, et al., hereby incorporated by reference. All other references referred to throughout this specification are hereby incorporated by reference.

While particular embodiments of this invention have been described, it will be obvious to those skilled in the art that various changes and modifications of this invention can be made without departing from the spirit and scope of the invention. It is intended to cover, in the appended claims, all such modifications that are within the scope of this invention.

What is claimed is:

1. A compound having the following structure:

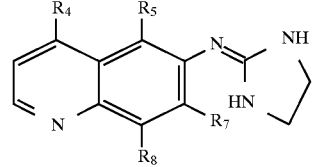

wherein:
(a) $R_4$ is selected from the group consisting of hydrogen; unsubstituted alkanyl or alkenyl having from 1 to about 3 carbon atoms; cycloalkyl; cycloalkenyl; methyl monosubstituted with hydroxy, thiol or amino; unsubstituted alkylthio or alkoxy having from 1 to about 3 carbon atoms; amino; unsubstituted amide; amido, unsubstituted or substituted with alkanyl or alkenyl having from 1 to about 3 carbon atoms; halo; unsubstituted sulfoxide; unsubstituted sulfonyl; and cyano;
(b) $R_5$ is unsubstituted alkanyl or alkenyl having from 1 to about 3 carbon atoms;
(c) $R_7$ is selected from hydrogen; unsubstituted $C_1$–$C_3$ alkanyl or alkenyl; hydroxy, thiol or amino; halo; and cyano;
(d) $R_8$ is selected from the group consisting of hydrogen; unsubstituted alkanyl or alkenyl having from 1 to about 3 carbon atoms; unsubstituted alkylthio or alkoxy having from 1 to about 3 carbon atoms; hydroxy; thiol; and halo.

2. A compound according to claim 1 wherein $R_7$ is hydrogen.

3. The compound of claim 2 wherein $R_4$ is selected from the group consisting of hydrogen, unsubstituted alkanyl or alkenyl having from 1 to about 3 carbon atoms, cycloalkyl, cycloalkenyl, unsubstituted alkylthio or alkoxy having from 1 to about 3 carbon atoms; cyano; amino; and halo.

4. The compound of claim 3 wherein $R_5$ is alkanyl, and $R_8$ is selected from the group consisting of methyl, methoxy, chloro and bromo.

5. The compound of claim 4 wherein $R_4$ is selected from the group consisting of hydrogen, methyl, ethyl, methoxy, cyano, chloro and fluoro.

6. The compound of claim 5 wherein $R_5$ is methyl.

7. The compound of claim 2 wherein both $R_5$ and $R_8$ are methyl.

8. The compound of claim 7 wherein $R_4$ is selected from the group consisting of hydrogen, cyano and fluoro.

9. The compound of claim 8 wherein $R_4$ is hydrogen.

10. The compound of claim 1 wherein:
$R_4$ is selected from the group consisting of hydrogen, methyl, ethyl, methoxy, cyano, chloro and fluoro;
$R_5$ is methyl, ethyl or cyclopropyl;
$R_7$ is methyl, chloro, fluoro or bromo; and
$R_8$ is hydrogen, methyl, chloro or bromo.

11. The compound of claim 10 wherein $R_4$ and $R_8$ are hydrogen, and $R_5$ and $R_7$ are methyl.

12. A pharmaceutical composition comprising:
(a) a safe and effective amount of a compound of any of claims 1, 2, 8, 9, 10 or 11 and
(b) a pharmaceutically-acceptable carrier.

13. A pharmaceutical composition according to claim 12 further comprising one or more actives chosen from the group consisting of an antihistamine, antitussive, mast cell stabilizer, leukotriene antagonist, expectorant/mucolytic, antioxidant or radical inhibitor, steroid, bronchodilator, antiviral, analgesic, antiinflammatory, gastrointestinal and ocular active.

14. A pharmaceutical composition according to claim 12 further comprising an antihistamine.

15. A pharmaceutical composition according to claim 12 further comprising an antiinflammatory.

16. A method for preventing or treating a disorder modulated by alpha-2 adrenoreceptors, by administering to a mammal in need of such treatment, a safe and effective amount of an alpha-2 adrenoreceptor agonist compound according to claim 1.

17. A method for preventing or treating a disorder modulated by alpha-2 adrenoreceptors, wherein the disorder is chosen from the groups comprising, nasal congestion, otitis media, sinusitis, asthma, pain, migraine, substance abuse and addiction, gastrointestinal disorder, ulcer, stomach hyperacidity, benign prostatic hypertrophy, by administering to a mammal in need of such treatment, a safe and effective amount of an alpha-2 adrenoreceptor agonist compound according to claim 1.

18. A method of treating or preventing nasal congestion by administering to a mammal in need of such treatment a safe and effective amount of a compound according to claim 1.

19. A method of treating or preventing nasal congestion by administering to a mammal in need of such treatment a safe and effective amount of a compound according to claims of any of claims 1, 8, 9 or 11.

20. The method of claim 17, wherein the disorder is otitis media.

21. The method of claim 17, wherein the disorder is sinusitis.

22. A method for preventing or treating a respiratory disorder, wherein the disorder is chosen from the group comprising cough, chronic obstructive pulmonary disease and asthma, by administering to a mammal in need of such treatment, a safe and effective amount of a compound according to claim 1.

23. A method for preventing or treating a respiratory disorder according to claim 22, wherein the disorder is asthma.

24. A method for preventing or treating disorders mediated by sympathetic activity and modulated by alpha-2 adrenoreceptors by administering to a mammal in need of such treatment, a safe and effective amount of an alpha-2 adrenoreceptor agonist compound according to claim 1.

25. A method of treating a disorder according to claim 24, wherein the disorder is chosen from the group comprising benign prostatic hypertrophy, myocardial ischemia, cardiac reperfusion injury, angina, cardiac arrhythmia, heart failure and hypertension.

26. The method of claim 25, wherein the disorder is heart failure.

27. A method for preventing or treating an ocular disorder modulated by alpha-2 adrenoreceptors, by administering to a mammal in need of such treatment, a safe and effective amount of a compound according to claim 1.

28. A method for preventing or treating an ocular disorder according to claim 27 wherein the disorder is chosen from the group comprising ocular hypertension, hyperemia, conjunctivitis, and uveitis and glaucoma.

29. A method for preventing or treating an ocular hypertensive disorder according to claim 28 wherein the disorder is glaucoma.

30. A method for preventing or treating a gastrointestinal disorder modulated by alpha-2 adrenoreceptors by administering to a mammal in need of such treatment, a safe and effective amount of an alpha-2 adrenoreceptor agonist compound according to claim 1.

31. A method for preventing or treating a gastrointestinal disorder, according to claim 30, wherein the disorder is chosen from the group comprising diarrhea and irritable bowel syndrome.

32. A method for preventing or treating a gastrointestinal disorder, according to claim 31, wherein the disorder is diarrhea.

33. A method for preventing or treating migraine by administering to a mammal in need of such treatment, a safe and effective amount of a compound according to claim 1.

34. A method for preventing or treating pain by administering to a mammal in need of such treatment, a safe and effective amount of a compound according to claim 1.

35. A method for treating substance abuse by administering to a mammal in need of such treatment, a safe and effective amount of a compound according to claim 1.

36. A compound having the following structure:

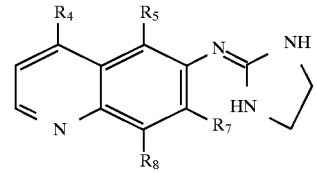

wherein:

(a) $R_4$ is selected from the group consisting of hydrogen; unsubstituted alkanyl or alkenyl having from 1 to about 3 carbon atoms; cycloalkyl; cycloalkenyl; methyl monosubstituted with hydroxy, thiol or amino; unsubstituted alkylthio or alkoxy having from 1 to about 3 carbon atoms; amino; unsubstituted amide; amido, unsubstituted or substituted with alkanyl or alkenyl having from 1 to about 3 carbon atoms; halo; unsubstituted sulfoxide; unsubstituted sulfonyl; and cyano;

(b) $R_5$ is unsubstitutod alkanyl or alkenyl having from 1 to about 3 carbon atoms;

(c) $R_7$ is selected from hydrogen; unsubstituted $C_1$–$C_3$ alkanyl or alkenyl; hydroxy, thiol or amino; halo; and cyano;

(d) $R_8$ is selected from the group consisting of hydrogen; unsubstituted alkanyl or alkenyl having from 1 to about 3 carbon atoms; unsubstituted alkylthio or alkoxy having from 1 to about 3 carbon atoms; hydroxy; thiol; and halo;

(e) provided that both $R_7$ and $R_8$ are not hydrogen.

* * * * *